United States Patent [19]
Shionozaki et al.

[11] Patent Number: 4,879,060
[45] Date of Patent: Nov. 7, 1989

[54] 2-PHENYLPYRIDINE DERIVATIVES AND LIQUID CRYSTAL COMPOSITIONS INCLUDING SAME

[75] Inventors: Yoshio Shionozaki; Hiroshi Mukai; Tsuyoshi Obikawa; Shuhei Yamada, all of Suwa, Japan

[73] Assignee: Seiko Epson Kabushiki Keisha, Tokyo, Japan

[21] Appl. No.: 68,996

[22] Filed: May 22, 1987

Related U.S. Application Data

[62] Division of Ser. No. 754,056, Jul. 11, 1985, Pat. No. 4,684,220.

[30] Foreign Application Priority Data

Jul. 12, 1984 [JP] Japan ................... 59-144848
Oct. 11, 1984 [JP] Japan ................... 59-213073
Mar. 27, 1985 [JP] Japan ................... 60-62553

[51] Int. Cl.⁴ .................. G02F 1/13; C09K 19/34; C07D 239/02; C07D 239/72; C07D 241/46
[52] U.S. Cl. .................. 252/299.61; 252/299.5; 350/333; 350/350 R; 350/350 S; 546/286; 546/287; 546/290; 546/300; 546/301; 546/330; 546/339; 546/348
[58] Field of Search .................. 252/299.61, 299.5; 350/350 R, 350 S, 333; 546/286, 287, 290, 300, 301, 330, 339, 348

[56] References Cited

U.S. PATENT DOCUMENTS

| | | | |
|---|---|---|---|
| 4,035,056 | 7/1987 | Coates et al. | 252/299.66 |
| 4,261,651 | 4/1981 | Grat et al. | 252/299.63 |
| 4,348,298 | 9/1982 | Zaschke et al. | 252/299.61 |
| 4,421,670 | 12/1983 | Deutscher et al. | 252/299.62 |
| 4,439,015 | 3/1984 | Rich et al. | 252/299.63 |
| 4,642,199 | 2/1987 | Sugimori et al. | 252/299.61 |
| 4,659,500 | 4/1987 | Sugimori et al. | 252/299.61 |
| 4,659,502 | 4/1987 | Fearon et al. | 252/299.61 |
| 4,668,425 | 5/1987 | Nigorikawa et al. | 252/299.61 |
| 4,668,426 | 5/1987 | Demus et al. | 252/299.61 |
| 4,684,220 | 8/1987 | Shionozaki et al. | 252/299.61 |
| 4,684,477 | 8/1987 | Sugimori et al. | 252/299.61 |

FOREIGN PATENT DOCUMENTS

| | | | |
|---|---|---|---|
| 58-121222 | 7/1983 | Japan | 252/299.63 |
| 60-149564 | 8/1985 | Japan | 252/299.61 |
| 1069413 | 4/1985 | U.S.S.R. | 252/299.61 |
| 1063101 | 6/1985 | U.S.S.R. | 252/299.61 |
| 2092169 | 8/1982 | United Kingdom | 252/299.61 |
| 2153345 | 8/1985 | United Kingdom | . |
| 1452826 | 10/1986 | United Kingdom | 252/299.66 |

OTHER PUBLICATIONS

Grachev, V. T. et al., Mol. Cryst. Liq. Cryst., vol. 65, pp. 133–144 (1981).

Pavluchenko, A. I., et al., Advances in Liquid Crystal Research and Applications, Bata, L.. Ed., Pergamon Press, Oxford, pp. 1007–1013 (1980).

Nash, J. A., et al., mol. Cryst. Liq. Cryst., vol. 25, pp. 299–321 (1974).

Grebyonkim, M. F., et al., Mol. Cryst. Liq. Cryst., vol. 124, pp. 245–257 (1985).

Pavluchenko, A. I., et al., Khim. Geterotsikl Soedim, vol. 10, pp. 1389–1391 (1985).

Schubert, H., Wiss. Z. Umiv. Halle XIX '70 m, H.S, 51–88.

Pavluchenko, A. I., et al., J. de Physique, Coll. C3, vol. 40, Suppl. No. 4, pp. C3 1–4 (Apr. 1979).

C.A. Service, Registry Handbook, Number section, 1983 Suppl, RN 85237-71-4.

Primary Examiner—Teddy S. Gron
Attorney, Agent, or Firm—Blum Kaplan

[57] ABSTRACT 2-phenylpyridine derivatives represented by the general formula:

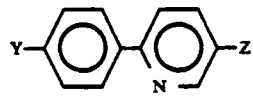

wherein when Y is R—, Z is one of R—, RO—, (Abstract continued on next page.)

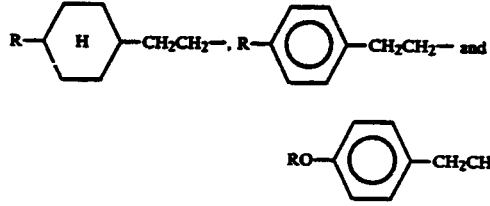

when Y is RO—, Z is one of straight chain pentyl,

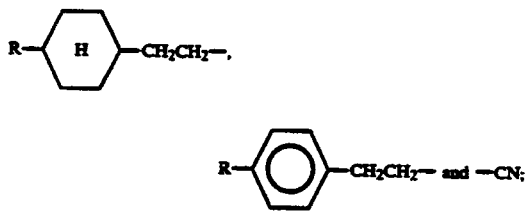

and —CN; and when Y is one of

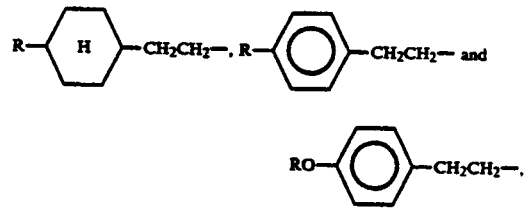

Z is one of R—, RO— and —CN; when Y is —CN, Z is one of RO—,

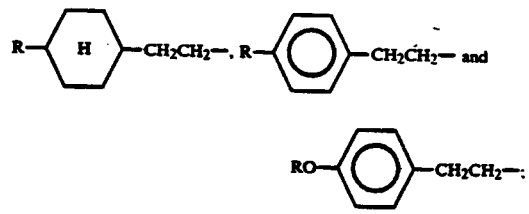

and R is a straight chain alkyl group from 1 to 12 carbon atoms, are disclosed. The 2-phenylpyridine derivatives in accordance with the invention are particularly well-suited for use in nematic liquid crystal compositions for reducing the steepness and response time of the liquid crystal compositions in a liquid crystal display device.

11 Claims, 7 Drawing Sheets

2-PHENYLPYRIDINE DERIVATIVES AND LIQUID CRYSTAL COMPOSITIONS INCLUDING SAME

This is a divisional of application Ser. No. 06/754,056, filed Jul. 11, 1985, now U.S. Pat. 4,684,220.

BACKGROUND OF THE INVENTION

This invention relates to 2-phenylpyridine derivatives, and more particularly to novel liquid crystal compositions including 2-phenylpyridine derivatives for use as electro-optical display materials.

Liquid crystal display devices have many advantages. The liquid crystal display unit including the driving circuitry is small and flat. It can be driven at low voltages with low power consumption. The displays do not cause eye strain for the user since the liquid crystal display is a passive element. In view of these advantages, the liquid crystal display devices have become widely used in various display devices, such as watches, electronic portable calculators and the like. This is particularly true recently as people have concentrated their focus on liquid crystal display devices to provide character display or graphic display for use in computer terminals and POS terminals in place of conventional cathode ray tubes. Accordingly, there is strong demand for greater capacity liquid crystal display devices.

Given this background, the multiplex driving method has become the most widely used with twisted nematic liquid crystal display devices (hereinafter "TN cell"). The multiplex driving method has been developed to enhance the performance of such liquid crystal display devices.

It is well known that the performance of the TN cell driven by the multiplex driving mode largely depends on the dynamic characteristics of the liquid crystal material used therein. It is necessary that the liquid crystal have a liquid crystal temperature range wide enough to cover fully the temperature range within which the TN cell will be used. To provide excellent electro-optical response, the liquid crystal must be colorless, must be chemically inert and electrically stable against heat and light. When considering the electro-optical response, visual dependence and the voltage-brightness of the TN cell and the steepness of the threshhold are particularly significant properties.

There are many compounds which are colorless and have stable properties. However, few of the existing compounds provide the desired liquid crystal temperature range and electro-optical response. Accordingly, it has been necessary to mix at least two nematic liquid crystal compounds together with additional non-nematic liquid crystal compounds in order to provide a liquid crystal composition suitable for use in a liquid crystal display device.

In order to provide high-density multiplex driving of a TN cell the following factors in the voltage-light transmittance property of the TN cell as illustrated in FIG. 1 are particularly significant:

Viewing Angle Dependency $\alpha = V_{50}\text{-}O90°/V_{50}\text{-}O50°$

Steepness of Response $\beta = V_{10}\text{-}O90°/V_{90}\text{-}O90°$ the smaller the above values of $\alpha$ and $\beta$ are, the more suitable the material is for use in the multiplex driving mode in a TN cell.

$\alpha$ and $\beta$ are closely related to the physical properties of the birefringence anisotropy ($\Delta n$) and the elastic constant $K_{33}/K_{11}$ of the liquid crystal material in the cell. Generally, by reducing the value of the product ($\Delta n\text{-}d$ of $\Delta n$ and the thickness of the liquid crystal layer (d), $\alpha$ is reduced and the applicable viewing angle is increased. However, if $\Delta n\text{-}d - 1.0\ \mu$ or less, the steepness $\beta$ deteriorates. Further, it is known that if $\Delta n\text{-}d$ is constant, as $K_{33}/K_{11}$ becomes small $\beta$ also becomes small. Based on this, B. S. Scheuble and G. Bauer in Japan Display '83, Proceedings of the 3rd International Display Research Conference, SID, p. 224, 1983, conducted measurement on known liquid crystal materials and identified the better performing liquid crystal compounds.

It is known that $\alpha$ and $\beta$ are influenced by the construction of the TN cell, such as the thickness of the cell (d) and the orientation of the panels therein. Moreover, when an improved device is required, a TN cell with improved properties is necessary. For example, if the display capacity is to be increased, a more steep threshhold property is required. Additionally, if the information display device is for out-door use, a much wider range of applicable viewing angle is necessary. Thus, at least an optimum value of the above-noted $\Delta n\text{-}d$ varies with the requirements of the display characteristics. Accordingly, the physical properties of standardized liquid crystal materials are not always suitably used in various TN cells.

Based on this technical background, it is desirable to provide an improved liquid crystal material suitable for use in a TN cell driven in the multiplex driving mode. It is particularly desirable to provide liquid crystal compounds to provide a desired $\alpha$ and $\beta$ by mixing the materials with each other or with other liquid crystal materials for use in TN cells. Such liquid crystal materials must be colorless, stable in all respects, easily mixed with existing nematic liquid crystal compounds or compositions in order to improve the properties, such as the liquid crystal temperature range and the electro-optical response.

SUMMARY OF THE INVENTION 2-phenylpyridine derivatives represented by the general formula:

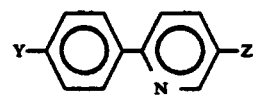

wherein Y and Z are as follows. When Y is R—, Z is one of R—, RO—,

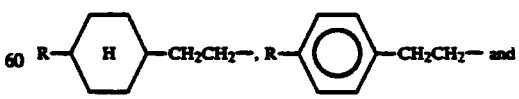

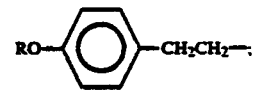

when Y is RO—, Z is one of straight chain pentyl,

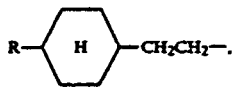

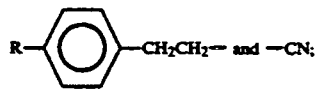

and when Y is one of

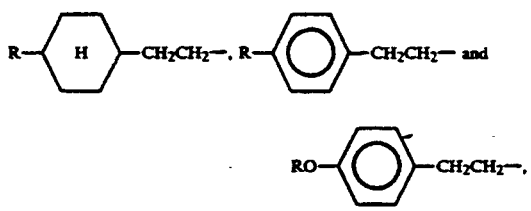

Z is one of R—, RO— and —CN; when Y is —CN, Z is one of RO—,

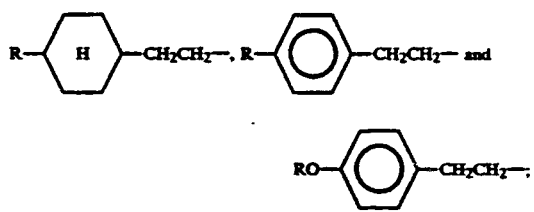

and R is a straight chain alkyl group from 1 to 12 carbon atoms.

The 2-phenylpyridine derivatives in accordance with the invention have suitable properties for improving multiplex driving mode thereby increasing the capacity of an electro-optical liquid crystal display device including a liquid crystal composition wherein the 2-phenylpyridine derivatives are included.

The 2-phenylpyridine derivatives are mixed with conventional nematic crystal compounds of the $N_a$ type having negative dielectric anisotropy and liquid crystal compounds of the $N_p$ type having positive dielectric anisotropy in order to improve the steepness and response speed of the compositions. Generally the 2-phenylpyridine derivative is included in an amount between about 2 to 80 weight percent based on a total weight of the composition.

Accordingly, it is an object of the invention to provide an improved liquid crystal compound.

It is another object of the invention to provide 2-phenylpyridine derivatives.

It is a further object of the invention to provide 2-phenylpyridine derivatives suitable for use as ingredients in liquid crystal compositions utilized as electro-optical display materials.

Still another object of the invention is to provide liquid crystal materials suitable for use in TN cells to reduce the viewing angle dependency and steepness of response.

Still a further object of the invention is to provide improved liquid crystal materials which may be mixed with known nematic liquid crystal compositions for improving the steepness and response speeds of the compositions.

Yet a further object of the invention is to provide a method for preparing improved 2-phenylpyridine derivatives.

Yet another object of the invention is to provide improved liquid crystal display devices including the new liquid crystal materials.

Still other objects and advantages of the invention will in part be obvious and will in part be apparent from the specification.

The invention accordingly comprises the several steps and the relation of one or more of such steps with respect to each of the others thereof, which will be exemplified in the composition method and device hereinafter disclosed, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 2:
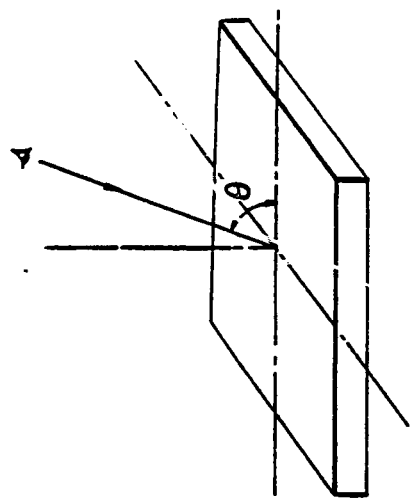
FIG. 2 illustrates the viewing angle O of the device of FIG. 1.
Figure 1:
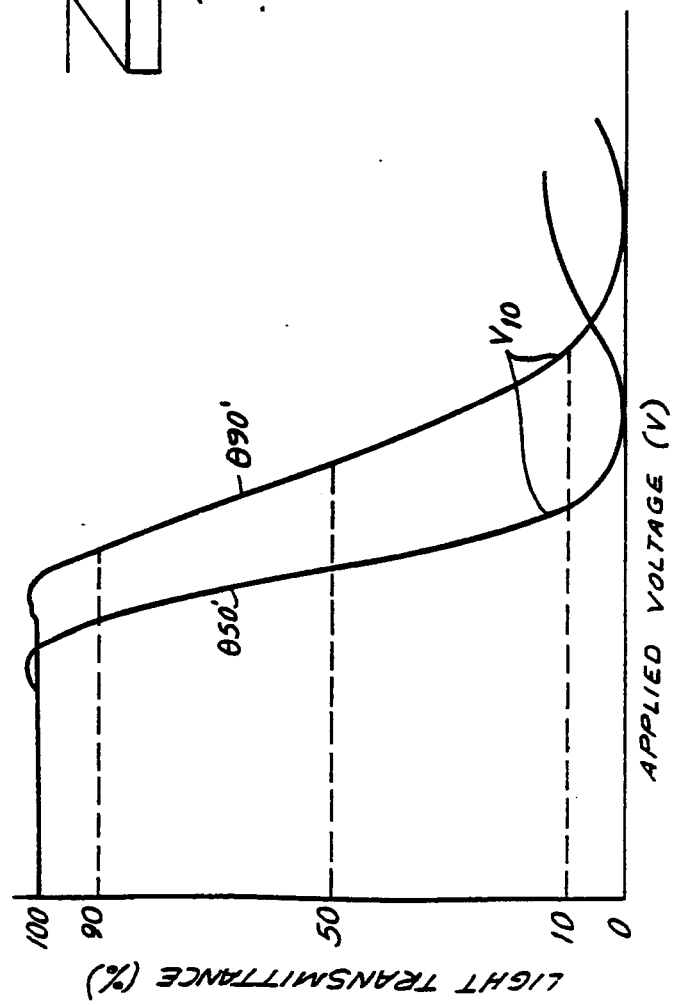
FIG. 1 illustrates the voltage-brightness characteristics of a twisted nematic liquid crystal display device.
Figure 3:
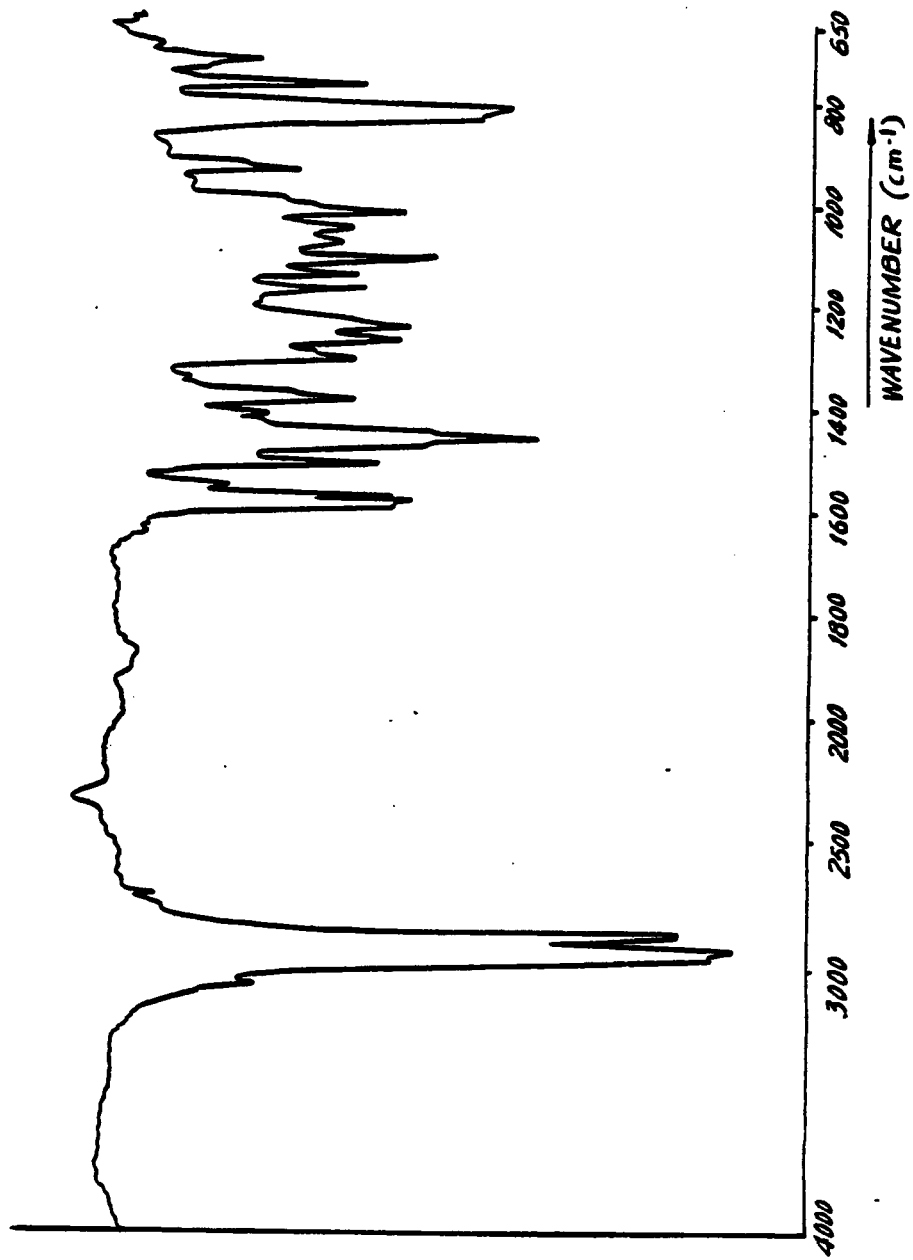
FIG. 3 shows the infrared adsorption spectrum of the 2-phenylpyridine derivative, 2-(4-hexyloxyphenyl)-5-pentylpyridine.
Figure 4:
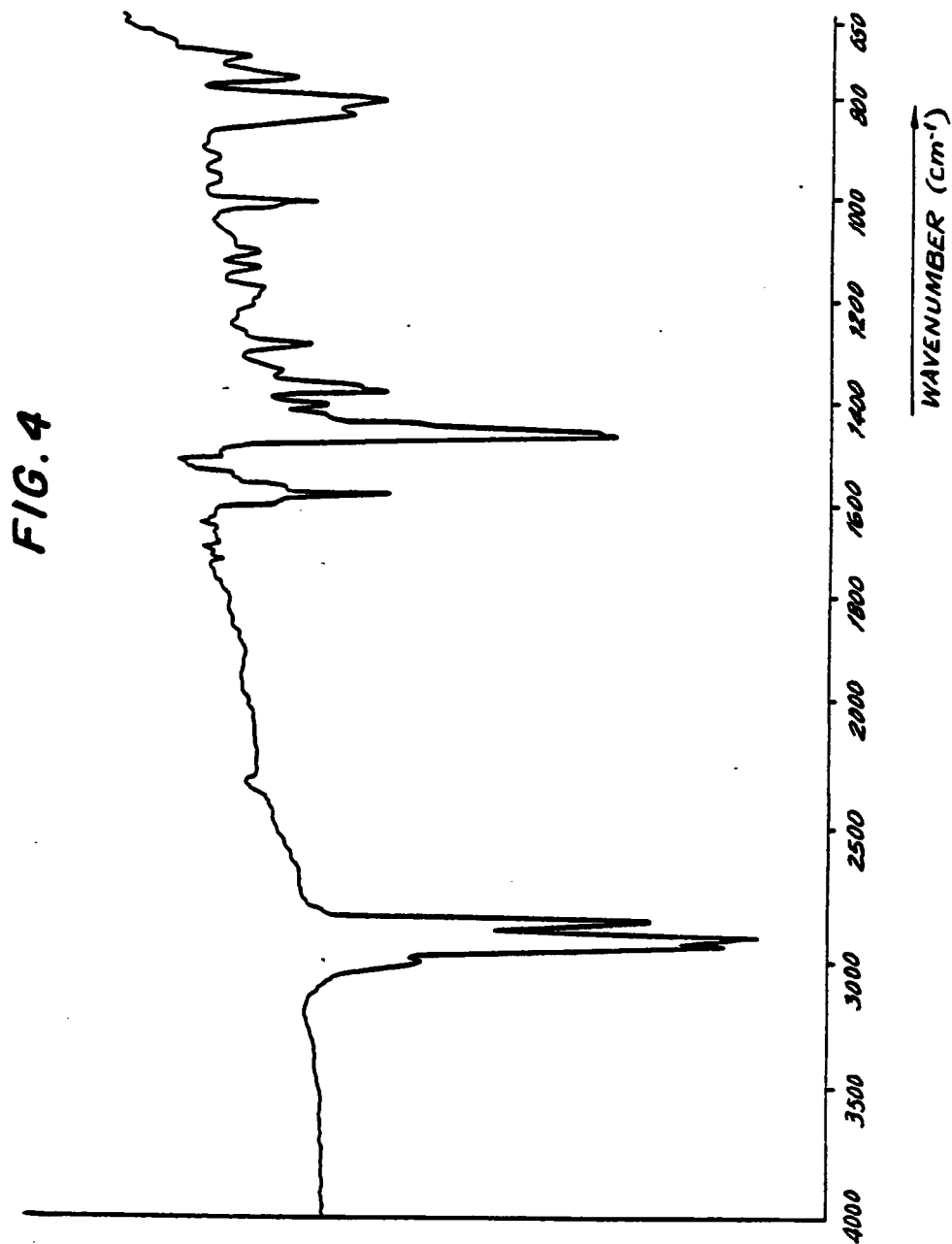
FIG. 4 illustrates the infrared adsorption spectrum of the 2-phenylpyridine derivative, 2-(4-pentylphenyl)-5-pentylpyridine.

The compounds in accordance with this invention are 2-phenylpyridine derivatives represented by the general formula as follows:

wherein, when Y is R—, Z is one of R—, RO—,

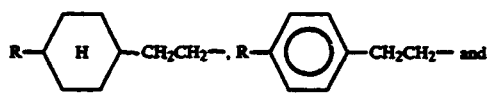

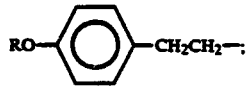

when Y is RO—, Z is one of straight chain pentyl,

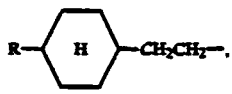

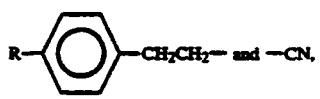

when Y is one of

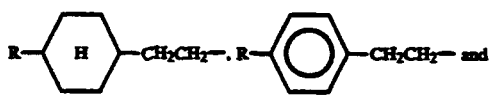

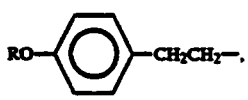

Z is one of R—, RO— and —CN; when Y is —CN, Z is one of RO—,

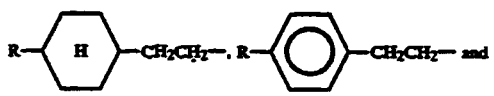

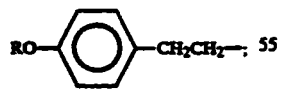

and R is straight chain alkyl having from 1 to 12 carbon atoms.

The 2-phenylpyridine compounds of this invention represented by the general formulae II to XX as follows are compounds not only having the multiplex characteristic required for a liquid crystal material to be used as an electro-optical display element, but also other characteristics required for at least some of the liquid crystal temperature range, dielectric anisotropy, reflectional anisotropy, viscosity and so on. Accordingly, the following compounds are particularly well suited for use in liquid crystal compositions.

  II

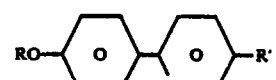  III

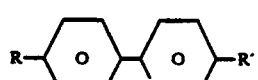  IV

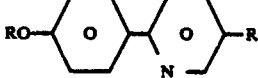  V

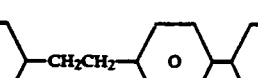  VI

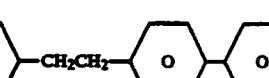  VII

  VIII

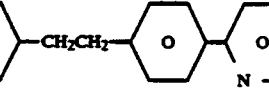  IX

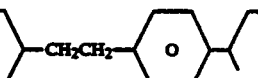  X

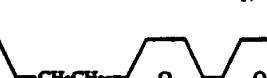  XI

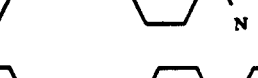  XII

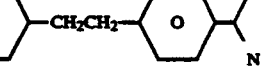  XIII

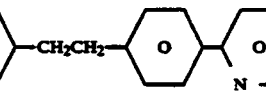  XIV

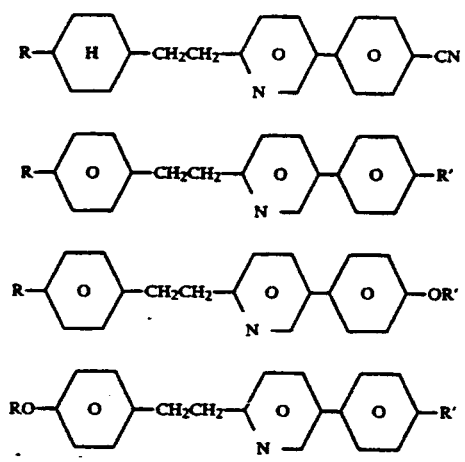
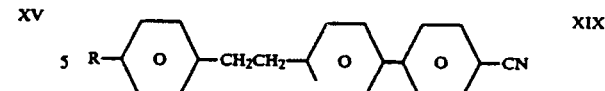
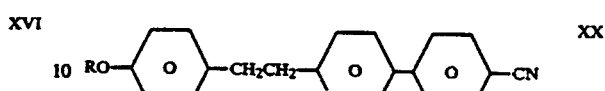
In the above general formulae, R and R' are straight chain alkyl.
The above compounds are prepared from arbitrarily selected p-substituted bromobenzene according to the reaction schemes as shown below based on the literature (C. S. Giam, J. L. Stout, Chem. Commum, 478, 1970):
<Scheme I>
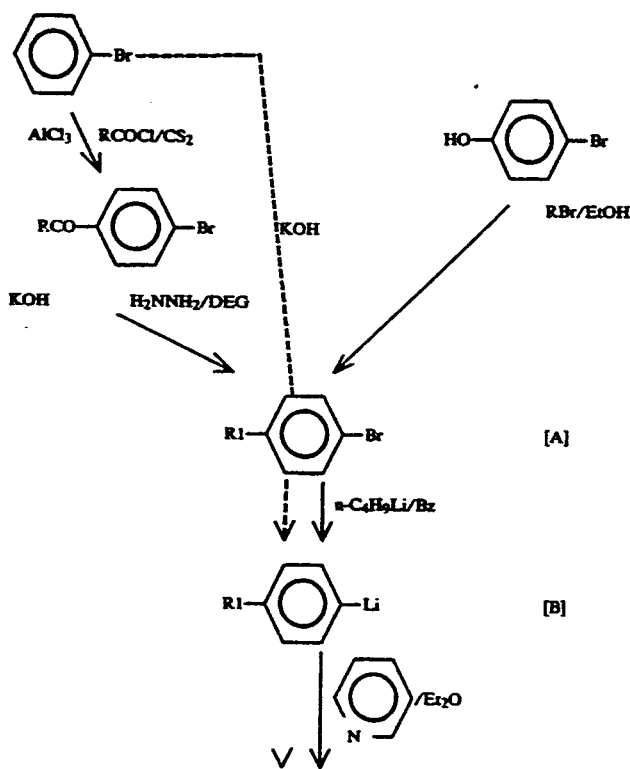

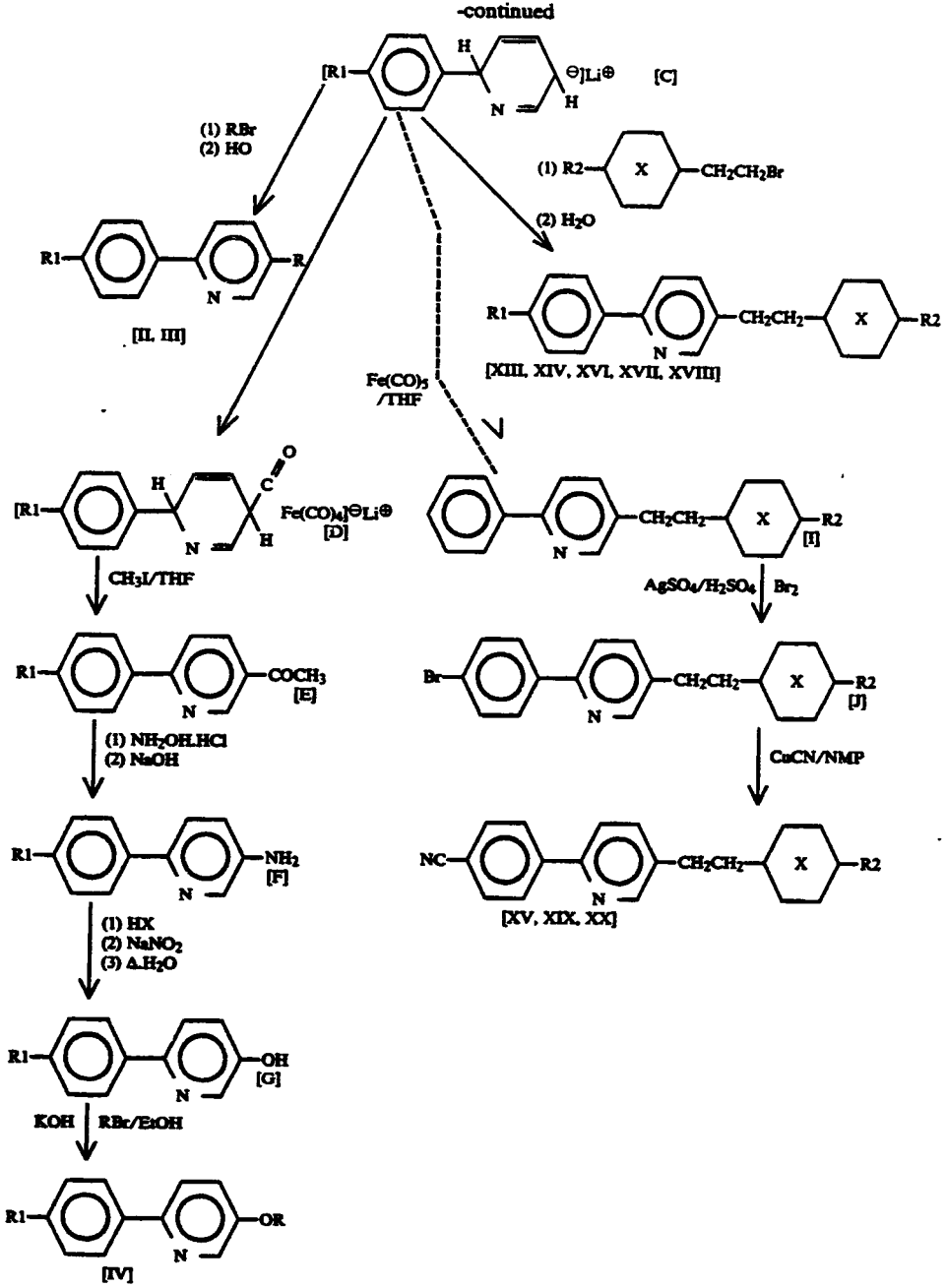
<Scheme II>
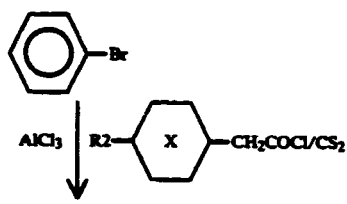

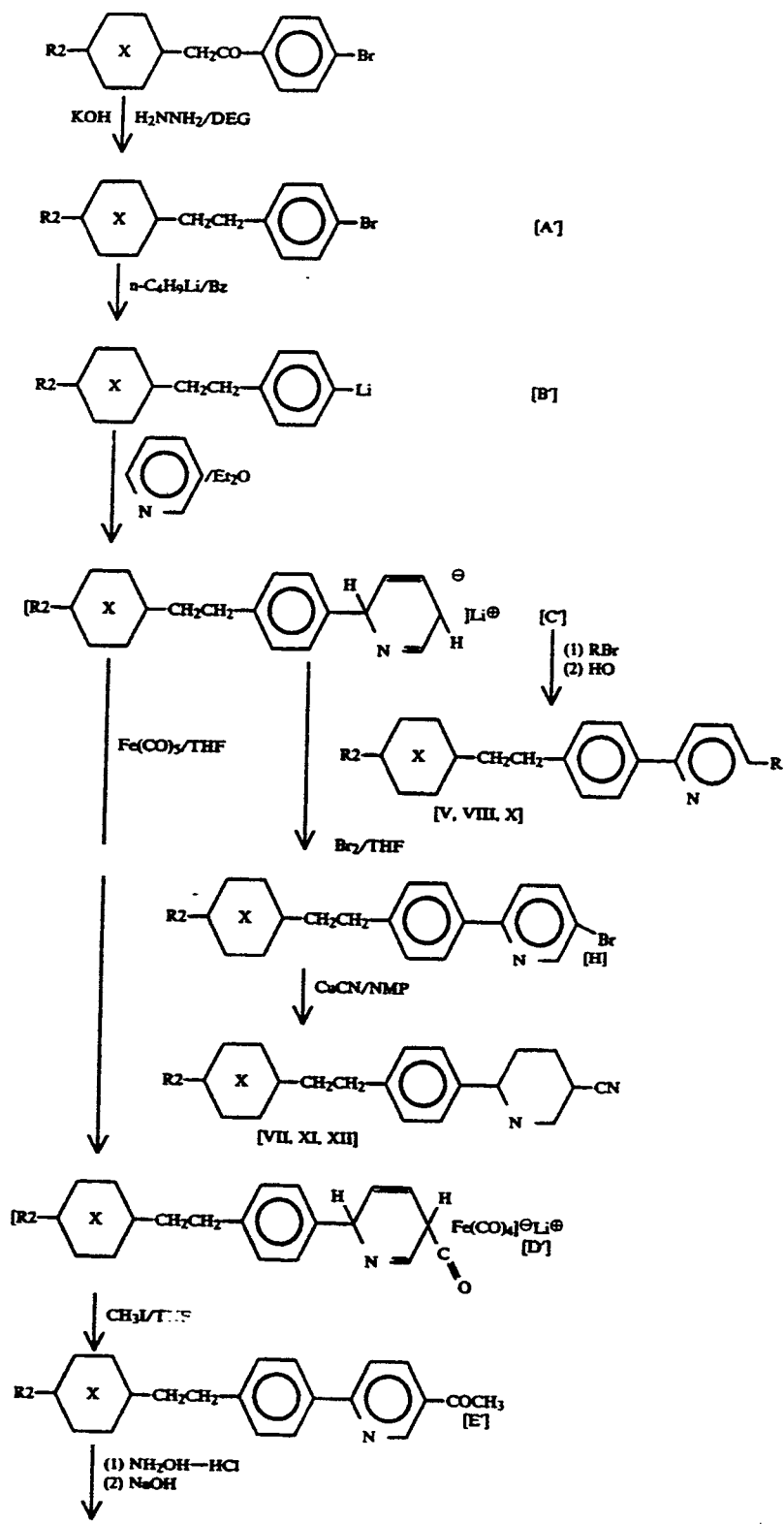

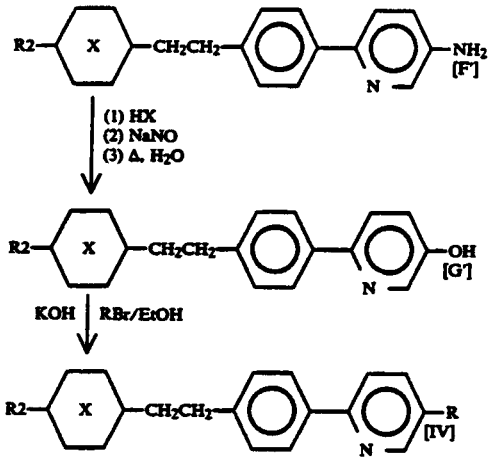

In the above schemes, R is alkyl, R1 and R2 are alkyl or alkoxy and

is 1,4-cyclohexylene or 1,4-phenylene.

The above reaction schemes are explained in outline below:

According to the above-mentioned C. S. Giam et al. method, in dry benzene, p-substituted phenyllithium is prepared from butyllithium and p-substituted bromobenzene (A, A' in the above scheme) such as bromobenzene and p-alkylbromobenzene, p-[2-trans-4'-alkyl-cyclohexyl)ethyl]bromobenzene, p-[2-(p'-alkylphenyl)ethyl]bromobenzene and p-[2-(p'-alkyoxyphenyl)ethyl]bromobenzene prepared from bromobenzene followed by a Friedel-Crafts acylation and a Wolff Kishner reduction, and p-alkoxybromobenzene prepared from p-bromophenol by Williamson reaction. The resulting p-substituted phenyllithium represented by the formula B or B' is dissolved in dry diethylether and is reacted with completely anhydrous pyridine to yield the intermediate represented by the formula C or C'.

The compound C or C' is reacted with 1-bromoalkane, 2-substituted bromoethane or bromine under appropriate conditions, respectively (each of the above reactions is carried out within the reaction system which is efficiently dried and efficiently substituted with the inactive gas), and the resulting compound is hydrolyzed to yield the compounds shown by the above molecular formulae II, III, V, VIII, X, XIII, XIV, XVI, XVII and XVIII and the formulae [H] and [I].

Alternatively, by cyanating compound [H] and compound [J] obtained by brominating compound [I] with bromine in silver sulfate/sulfuric acid, respectively, using cuprous cyanide by the well known method, the compounds represented by the molecular formulae VII, XI, XII, XV, XIX and XX are obtained.

The compound C or C' is reacted with iron pentacarbonyl under appropriate conditions to yield the intermediate shown by the formula D or D'. Then the compound E or E' obtained by reacting the intermediate D or D' and methyl iodide under appropriate conditions is treated with hydroxylamine hydrochloric acid salt by Beckmann's transformation reaction to yield the amino compound of F or F'. The compound F or F' is diazoated and reacted by Sandmeyer's reaction to yield the compound G or G'. Then the compound G or G' is reacted with 1-bromoalkane by Williamson's reaction to yield the compounds as shown by the molecular formulae IV, VI and IX.

Most of the compounds obtained as above in accordance with this invention are liquid crystal compounds which present the nematic or smectic phase, which are colorless and very stable chemically and electrically against heat and light.

Furthermore, the compounds in accordance with this invention are mutually soluble with one another or with other nematic liquid crystal compounds or liquid crystal compositions, thereby easily composing new liquid crystal compositions.

The following Examples are set forth by way of illustration to show preparation of the compounds in accordance with the invention. They are set forth for purposes of illustration only, and not intended in a limiting sense.

EXAMPLE 1

50.0g (0.290mol) of p-bromophenyl was dissolved in 300ml of ethanol and 14.2g (0.340mol) of sodium hydroxide and 49.5g (0.300mol) of 1-bromohexane were added thereto. The resulting solution was stirred at 70° C. for 4 hours to complete the reaction and the solvent was removed by distillation. Then 150ml of water was added and the organic layer was extracted with 200ml of hexane. The hexane was removed by distillation thereafter. The residue was distilled under reduced pressure to yield 63.4g of 4-hexyloxybromobenzene having a b.p. 139° C./7mmHg.

24.0g (0.093mol) of 4-hexyloxybromobenzene was dissolved in 30ml of benzene and stirred at room temperature in a stream of nitrogen. To the resulting solution was added drop-wise 50ml of hexane solution including 15% of butyllithium was added drop-wise for 30 minutes and the solution was maintained under stirring for 2 hours. The produced precipitate gathered by filtration in a stream of nitrogen was dried under reduced pressure to yield 11.1g of 4-hexyloxyphenyllithium.

11.1g (0.060mol) of 4-hexyloxyphenyllithium was dissolved in 100ml of diethylether under a stream of nitrogen. Then 5.1g (0.065mol) of pyridine was added drop-wise with stirring at 5° C. or lower for 30 minutes. Then the temperature was raised to room temperature and the solution was maintained under stirring for 3 hours.

The reaction solution was chilled to −5° C. and stirred in a stream of nitrogen. 9.5g (0.063mol) of 1-bromopentane dissolved in 100ml of tetrahydrofuran was added drop-wise for 20 minutes. Then the temperature was raised to room temperature and the solution was kept stirred for 40 minutes.

200ml of water was added to the reaction solution and the solution was stirred for a while. The ether layer was separated and the ether was removed by distillation. The residue was distilled under reduced pressure. The fraction having the boiling point of 210° to 225° C./3mmHg was recrystallized from ethanol to yield 4.4g of 2-(4-hexyloxyphenyl)-5-pentylpyridine.

The transition temperature of this compound was as below:

C⇌N 64.5° C., N⇌I 72.0° C.

(C is the crystalline phase, N is the nematic phase and I is the isotropic liquid phase. The same marks are used hereinafter and X is the smectic phase.)

The following are other examples of compounds in accordance with this embodiment of the invention which may be prepared following the procedures of Example 1:

2-(4-ethyloxyphenyl)-5-pentylpyridine

C→N 60.5° C., C←N 47.0° C., N⇌I 62.0° C.

2-(4-butyloxyphenyl)-5-pentylpyridine

C→N 60.0° C., N⇌I 65.0° C.

2-(4-pentyloxyphenyl)-5-pentylpyridine

C⇌N 55.5° C., N⇌I 62.0° C.

2-(4-propyloxyphenyl)-5-pentylpyridine 2-(4-heptyloxyphenyl)-5-pentylpyridine

C→S 56.9° C., S⇌N 61.8° C., N⇌I 68.2° C.

2-(4-octyloxyphenyl)-5-pentylpyridine 2-(4-heptyloxyphenyl)-5-octylpyridine

EXAMPLE 2

Step 1—1

104.5g (0.76mol) of anhydrous aluminum chloride and 92.1g (0.76mol) of valeroylchloride were added to 350ml of carbon disulfide chilled at 0° C. To the resulting mixture with chilling and stirring, 100g (0.64mol) of bromobenzene was added and the solution was stirred at room temperature for 24 hours. After completion of the reaction, the resulting mixture was added to 400ml of cold 4N hydrochloric acid and the aluminum chloride complex was decomposed. Then the organic layer was extracted with chloroform and washed with water and the solvent was removed by distillation. The residue was distilled under reduced pressure to yield 95g of 4-pentanoylbromobenzene having a b.p. 105° to 110° C./2mmGn.

Step 1-2

95g (0.39mol) of 4-pentanoylbromobenzene, 300ml of diethyleneglycol, 40ml (0.80mol) of 100% hydradine hydrate and 45g (0.80mol) of potassium hydroxide were heated at 130° C. for 1 hour and then at 180° C. with stirring for 3 hour. Water was added to the reaction solution and the organic layer was extracted with chloroform. After washing the extracted layer with water, the chloroform was removed by distillation. Then the residue was distilled under reduced pressure to yield 75.4g of 4-pentylbromobenzene having at b.p. 87° to 90° C./2mmHg.

18.35g (0.081mol) of 4-pentylbromobenzene was dissolved in 30ml of benzene and the solution was stirred at room temperature in a stream of nitrogen. To the resulting solution was added drop-wise 50ml (0.081mol) of hexane solution including 15% butyllithium for 30 minutes and the solution was stirred for 2 hours. Then the produced precipitate gathered by the filtration in a stream of nitrogen was dried under reduced pressure to yield 9.2g of 4-pentylphenyllithium.

Step 3-1

9.2g (0.06mol) of 4-pentylphenyllithium was dissolved in 100ml of diethylether in the nitrogen air flow and 5.1g (0.065mol) of pyridine was added for 30 minutes at 5° C. or lower with stirring. Then the temperature was raised to room temperature and the solution was stirred for 3 hours.

Step 3-2

The reaction solution was chilled to −5° C. and stirred. Then 9.5g (0.063mol) of 1-bromopentane dissolved in 100ml of tetrahydrofuran was added drop-wise for 20 minutes. Then the temperature was raised to room temperature and the solution was stirred for 40 minutes.

Step 3—3

200ml of water was added to the reaction solution and the solution was stirred for a while. The ether layer was separated and ether was removed by distillation and the residue was distilled under reduced pressure. The fraction having a boiling point of 190° to 205° C./2mmHg was recrystallized from ethanol to yield 2.6g of 2-(4-pentylphenyl)-5-pentylpyridine.

The phase transition temperature of this compound was:

C→I 33° C., I→S 32° C., S→C 9° C.

The following are other examples of the compounds in accordance with this embodiment of the invention which may be prepared following the procedures of Example 2:

2-(4-propylphenyl)-5-ethylpyridine
2-(4-butylphenyl)-5-ethylpyridine
2-(4-pentylphenyl)-5-ethylpyridine 2-(4-hexylphenyl)-5-ethylpyridine
2-(4-heptylphenyl)-5-ethylpyridine
2-(4-octylphenyl)-5-ethylpyridine
2-(4-propylphenyl)-5-propylpyridine
2-(4-butylphenyl)-5-propylpyridine
2-(4-pentylphenyl)-5-propylpyridine
2-(4-hexylphenyl)-5-propylpyridine
2-(4-heptylphenyl)-5-propylpyridine
2-(4-octylphenyl)-5-propylpyridine
2-(4-ethylphenyl)-5-butylpyridine
2-(4-propylphenyl)-5-butylpyridine
2-(4-butylphenyl)-5-butylpyridine
2-(4-pentylphenyl)-5-butylpyridine
2-(4-hexylphenyl)-5-butylpyridine
2-(4-heptylphenyl)-5-butylpyridine
2-(4-octylphenyl)-5-butylpyridine
2-(4-ethylphenyl)-5-pentylpyridine
2-(4-propylphenyl)-5-pentylpyridine
2-(4-butylphenyl)-5-pentylpyridine

C—I 42° C.

2-(4-hexylphenyl)-5-pentylpyridine
2-(4-heptylphenyl)-5-pentylpyridine
2-(4-octylphenyl)-5-pentylpyridine
2-(4-ethylphenyl)-5-hexylpyridine
2-(4-propylphenyl)-5-hexylpyridine
2-(4-butylphenyl)-5-hexylpyridine
2-(4-pentylphenyl)-5-hexylpyridine
2-(4-hexylphenyl)-5-hexylpyridine
2-(4-heptylphenyl)-5-hexylpyridine
2-(4-octylphenyl)-5hexylpyridine

C—S 38° C., S—I 60.5° C.

2-(4-ethylphenyl)-5-heptylpyridine
2-(4-propylphenyl)-5-heptylpyridine
2-(4-butylphenyl)-5-heptylpyridine
2-(4-pentylphenyl)-5-heptylpyridine

C—S 31.5° C., S=I 6.5° C., S—C 4.0° C.

2-(4-hexylphenyl)-5-heptylpyridine
2-(4-heptylphenyl)-5-heptylpyridine
2-(4-octylphenyl)-5-heptylpyridine
2-(4-ethylphenyl)-5-heptylpyridine
2-(4-ethylphenyl)-5-octylpyridine
2-(4-propylphenyl)-5-octylpyridine
2-(4-butylphenyl)-5-octylpyridine
2-(4-pentylphenyl)-5-octylpyridine

C—S 37.5° C., S—I 52° C., I—S 8° C.

2-(4-hexylphenyl)-5-octylpyridine
2-(P-heptylphenyl)-5-octylpyridine
2-(P-octylphenyl)-5-octylpyridine

EXAMPLE 3

Diethylether solution including the reaction product of 18.4g of new p-pentylphenyllithium obtained by the procedure of Example 2 and 10.2g of pyridine was chilled to —65° C. To this solution under stirring was added drop-wise 500ml of dry tetrahydrofuran solution in which 128g of iron pentacarbonyl was dissolved. Then the temperature of the solution was raised to room temperature and the solution was stirred for 1 hour. While chilling and stirring the resulting solution, 1.8g of methyl iodide/10ml of tetrahydrofuran was added drop-wise for 30 minutes and stirred. Following the completion of the reaction, 200ml of water was added and stirred and the major portion of ether and tetrahydrofuran was removed by distillation. The residue was washed with warm water several time, dried and distilled under reduced pressure. The fraction having a boiling point of 170° to 185° C./2mmHg was collected and recrystallized from methanol.

9g of the resulting 2-(p-pentylphenyl)-5-acetylpyridine was mixed with 3.7g of hydroxyiamine hydrochloric acid salt, 70ml of 85% phosphoric acid and 30ml or polyphosphoric acid. The mixture was heated to 160° C. for 3 hours with stirring. Following completion of the reaction, the resulting mixture was injected onto 200g of ice and the deposited crystals were filtered. Then the crystals were washed with water several times and placed into a solution of 16.8g of sodium hydroxide/100ml of water stirred for 3 hours. The crystals were again filtered and fully washed with water and dried. The resulting crystals were distilled under reduced pressure to obtain the fraction having a boiling point of 170° to 175° C./2mmHg.

3.2g of the resulting 2-(p-pentylphenyl)-5-aminopyridine was mixed with 30ml of 20% sulfuric acid to yield sulfuric acid salt. To this mixture with chilling (maintain at 0° to 5° C.) and stirring, a solution of 1.4g of sodium nitride/3ml of water was added drop-wise. After completion of the reaction, a small amount of urea was added and the solution was stirred. Then the insoluble matter was removed from the resulting solution by filtration to yield diazonium salt solution. This solution was heated to about 70° C. for 1 hour and then the crystals separated by chilling were filtered. The crystals were fully washed with water and recrystallized from hexane.

2.8g of the resulting 2-(p-pentylphenyl)-5-hydroxypyridine, 2g of 1-bromobutane and 0.8g of potassium hydroxide placed in 60ml of ethanol were heated under reflux for 4 hours. The potassium bromide precipitated during the reaction was removed by filtration. The ethanol was removed by distillation. The residue was extracted with diethylether and the ether layer was washed with water several times and then the ether was removed by distillation. The residue was distilled under reduced pressure. The collected fraction having a boiling point of 185° to 187° C./2mmHg was recrystallized from methanol to yield 1.7g of 2-(p-pentylphenyl)-5-butyloxypyridine.

The phase transition temperature of this compound was as follows:

C—I 38° C., I—S 34° C.

The following are other examples of the compounds in accordance with this embodiment of the invention which may be prepared following the procedures of Example 3:

2-(p-propylphenyl)-5-ethoxypyridine
2-(p-propylphenyl)-5-propyloxypyridine
2-(p-propylphenyl)-5-butyloxypyridine
2-(p-propylphenyl)-5-pentyloxypyridine
2-(p-propylphenyl)-5-hexyloxypyridine
2-(p-propylphenyl)-5-heptyloxypyridine
2-(p-butylpenyl)-5-ethoxypyridine

C—I 29.5° C.

2-(p-butylphenyl)-5-propyloxypyridine
2-(p-butylphenyl)-5-butyloxypyridine 2-(p-butylphenyl)-5-pentyloxypyridine
2-(p-butylphenyl)-5-hexyloxypyridine
2-(p-butylphenyl)-5-heptyloxypyridine
2-(p-butylphenyl)-5-octyloxypyridine
2-(p-pentylphenyl)-5-ethoxypyridine
2-(p-pentylphenyl)-5-propyloxypyridine

C—I 42° C.

2-(p-pentylphenyl)-5-butyloxypyridine
2-(p-pentylphenyl)-5-pentyloxypyridine
2-(p-pentylphenyl)-5-hexyloxypyridine
2-(p-pentylphenyl)-heptyloxypyridine
2-(p-pentylphenyl)-octyloxypyridine
2-(p-hexylphenyl)-ethoxypyridine
2-(p-hexylphenyl)-propyloxypyridine
2-(p-hexylphenyl)-butyloxypyridine

C—S 26° C., S—I 44.5° C.

2-(p-hexylphenyl)-pentyloxypyridine
2-(p-hexylphenyl)-hexyloxypyridine
2-(p-hexylphenyl)-heptyloxypyridine
2-(p-hexylphenyl)-octyloxypyridine
2-(p-heptylphenyl)-5-ethoxypyridine
2-(p-heptylphenyl)-5-propyloxypyridine
2-(p-heptylphenyl)-5-butyloxypyridine
2-(p-heptylphenyl)-5-pentyloxypyridine
2-(p-heptylphenyl)-5-hexyloxypyridine
2-(p-heptylphenyl)-5-heptyloxypyridine
2-(p-heptylphenyl)-5-octylpyridine
2-(p-octylphenyl)-5-ethoxypyridine
2-(p-octylphenyl)-5-propyloxypyridine
2-(p-octylphenyl)-5-butyloxypyridine
2-(p-octylphenyl)-5-pentyloxypyridine
2-(p-octylphenyl)-5-hexyloxypyridine
2-(p-octylphenyl)-5-heptyloxypyridine
2-(p-octylphenyl)-5-heptyloxypyridine
2-(p-octylphenyl)-5-octyloxypyridine

EXAMPLE 4

A solution of 100ml of tetrahydrofuran including 14g of 2-(trans-4'-propylcyclohexyl)-1-bromoethane was added drop-wise to a diethylether solution including 9.2g of p-pentylphenyllithium obtained by the same procedure described in Example 2 and 5.1 of pyridine. The resulting solution was processed in the same way as Examples 1 and 2 to yield 8.5g of 2-(p-pentylphenyl)-5-[2'-trans-4"'-propylcyclohexyl)ethyl]pyridine.

The phase transition temperature of this compound was:

C—S 137.5° C., S—I 159.5° C.

The following are other examples of the compounds in accordance with this embodiment of the invention which may be prepared following the procedure of Example 4:

2-(p-ethylphenyl)-5-[2'-(trans-4"'-propylcyclohexyl)ethyl]pyridine
2-(p-ethylphenyl)-5-[2'-(trans-4"'-butylcyclohexyl)ethyl]pyridine
2-(p-ethylphenyl)-5-[2'-(trans-4"'-pentylcyclohexyl)ethyl]pyridine
2-(p-ethylphenyl)-5-[2'-(trans-4"'-hexylcyclohexyl)ethyl]pyridine
2-(p-propylphenyl)-5-[2'-(trans-4"'-ethylcyclohexyl)ethyl]pyridine
2-(p-propylphenyl)-5-[2'-(trans-4"'-propylcyclohexyl)ethyl]pyridine
2-(p-propylphenyl)-5-[2'-(trans-4"'-butylcyclohexyl)ethyl]pyridine
2-(p-propylphenyl)-5-[2'-(trans-4"'-pentylcyclohexyl)ethyl]pyridine
2-(p-propylphenyl)-5-[2'-(trans-4"'-hexylcyclohexyl)ethyl]pyridine
2-(p-butylphenyl)-5-[2'-(trans-4"'-ethylcyclohexyl)ethyl]pyridine
2-(p-butylphenyl)-5-[2'-(trans-4"'-propylcyclohexyl)ethyl]pyridine
2-(p-butylphenyl)-5-[2'-(trans-4"'-butylcyclohexyl)ethyl]pyridine
2-(p-butylphenyl)-5-[2'-(trans-4"'-pentylcyclohexyl)ethyl]pyridine
2-(p-butylphenyl)-5-[2'-(trans-4"'-hexylcyclohexyl)ethyl]pyridine
2-(p-pentylphenyl)-5-[2'-(trans-4"'-ethylcyclohexyl)ethyl]pyridine
2-(p-pentylphenyl)-5-[2'-(trans-4"'-butylcyclohexyl)ethyl]pyridine
2-(p-pentylphenyl)-5-[2'-(trans-4"'-pentylcyclohexyl)ethyl]pyridine
2-(p-pentylphenyl)-5-[2'-(trans-4"'-hexylcyclohexyl)ethyl]pyridine
2-(p-hexylphenyl)-5-[2'-(trans-4"'-ethylcyclohexyl)ethyl]pyridine
2-(p-hexylphenyl)-5-[2'-(trans-4"'-propylcyclohexyl)ethyl]pyridine

C—S 127° C., S—I 151° C.

2-(p-hexylphenyl)-5-[2'-(trans-4"'-butylcyclohexyl)ethyl]pyridine

C—S 139.5° C., S—I 155° C.

2-(p-hexylphenyl)-5-[2'-(trans-4"'-pentylcyclohexyl)ethyl]pyridine
2-(p-hexylphenyl)-5-[2'-(trans-4"'-hexylcyclohexyl)ethyl]pyridine
2-(p-ethoxyphenyl)-5-[2'-(trans-4"'-ethylcyclohexyl)ethyl]pyridine
2-(p-ethoxyphenyl)-5-[2'-(trans-4"'-propylcyclohexyl)ethyl]pyridine
2-(p-ethoxyphenyl)-5-[2'-(trans-4"'-butylcyclohexyl)ethyl]pyridine
2-(p-ethoxyphenyl)-5-[2'-(trans-4"'-pentylcyclohexyl)ethyl]pyridine
2-(p-ethoxyphenyl)-5-[2'-(trans-4"'-hexylcyclohexyl)ethyl]pyridine
2-(p-propyloxyphenyl)-5-[2'-(trans-4"'-ethylcyclohexyl)ethyl]pyridine
2-(p-propyloxyphenyl)-5-[2'-(trans-4"'-propylcyclohexyl)ethyl]pyridine
2-(p-propyloxyphenyl)-5-[2'-(trans-4"'-butylcyclohexyl)ethyl]pyridine
2-(p-propyloxyphenyl)-5-[2'-(trans-4"'-pentylcyclohexyl)ethyl]pyridine
2-(p-propyloxyphenyl)-5-[2'-(trans-4"'-hexylcyclohexyl)ethyl]pyridine
2-(p-butyloxyphenyl)-5-[2'-(trans-4"'-ethylcyclohexyl)ethyl]pyridine
2-(p-butyloxyphenyl)-5-[2'-(trans-4"'-propylcyclohexyl)ethyl]pyridine
2-(p-butyloxyphenyl)-5-[2'-(trans-4"'-butylcyclohexyl)ethyl]pyridine 2-(p-butyloxyphenyl)-5-[2'-(trans-4''-pentylcyclohexyl)ethyl]pyridine
2-(p-butyloxyphenyl)-5-[2'-(trans-4''-hexylcyclohexyl)ethyl]pyridine
2-(p-pentyloxyphenyl)-5-[2'-(trans-4''-ethylcyclohexyl)ethyl]pyridine
2-(p-pentyloxyphenyl)-5-[2'-(trans-4''-propylcyclohexyl)ethyl]pyridine
2-(p-pentyloxyphenyl)-5-[2'-(trans-4''-butylcyclohexyl)ethyl]pyridine
2-(p-pentyloxyphenyl)-5-[2'-(trans-4''-pentylcyclohexyl)ethyl]pyridine
2-(p-pentyloxyphenyl)-5-[2'-(trans-4''-hexylcyclohexyl)ethyl]pyridine
2-(p-hexyloxyphenyl)-5-[2'-(trans-4''-ethylcyclohexyl)ethyl]pyridine
2-(p-hexyloxyphenyl)-5-[2'-(trans-4''-propylcyclohexyl)ethyl]pyridine
2-(p-hexyloxyphenyl)-5-[2'-(trans-4''-butylcyclohexyl)ethyl]pyridine
2-(p-hexyloxyphenyl)-5-[2'-(trans-4''-pentylcyclohexyl)ethyl]pyridine
2-(p-hexyloxyphenyl)-5-[2'-(trans-4''-hexylcyclohexyl)ethyl]pyridine
2-(p-ethylphenyl)-5-[2'-(p'-ethylphenyl)ethyl]pyridine
2-(p-ethylphenyl)-5-[2'-(p'-propylphenyl)ethyl]pyridine
2-(p-ethylphenyl)-5-[2'-(p'-butylphenyl)ethyl]pyridine
2-(p-ethylphenyl)-5-[2'-(p'-pentylphenyl)ethyl]pyridine
2-(p-ethylphenyl)-5-[2'-(p'-hexylphenyl)ethyl]pyridine
2-(p-propylphenyl)-5-[2'-(p'-ethylphenyl)ethyl]pyridine
2-(p-propylphenyl)-5-[2'-(p'-propylphenyl)ethyl]pyridine
2-(p-propylphenyl)-5-[2'-(p'-butylphenyl)ethyl]pyridine
2-(p-propylphenyl)-5-[2'-(p'-pentylphenyl)ethyl]pyridine
2-(p-propylphenyl)-5-[2'-(p'-hexylphenyl)ethyl]pyridine
2-(p-butylphenyl)-5-[2'-(p'-ethylphenyl)ethyl]pyridine
2-(p-butylphenyl)-5-[2'-(p'-propylphenyl)ethyl]pyridine
2-(p-butylphenyl)-5-[2'-(p'-butylphenyl)ethyl]pyridine
2-(p-butylphenyl)-5-[2'-(p'-pentylphenyl)ethyl]pyridine
2-(p-butylphenyl)-5-[2'-(p'-hexylphenyl)ethyl]pyridine
2-(p-pentylphenyl)-5-[2'-(p'-ethylphenyl)ethyl]pyridine
2-(p-pentylphenyl)-5-[2'-(p'-propylphenyl)ethyl]pyridine
2-(p-pentylphenyl)-5-[2'-(p'-butylphenyl)ethyl]pyridine
2-(p-pentylphenyl)-5-[2'-(p'-pentylphenyl)ethyl]pyridine
2-(p-pentylphenyl)-5-[2'-(p'-hexylphenyl)ethyl]pyridine
2-(p-hexylphenyl)-5-[2'-(p'-ethylphenyl)ethyl]pyridine
2-(p-hexylphenyl)-5-[2'-(p'-propylphenyl)ethyl]pyridine
2-(p-hexylphenyl)-5-[2'-(p'-butylphenyl)ethyl]pyridine
2-(p-hexylphenyl)-5-[2'-(p'-pentylphenyl)ethyl]pyridine
2-(p-hexylphenyl)-5-[2'-(p'-hexylphenyl)ethyl]pyridine
2-(p-ethoxyphenyl)-5-[2'-(p'-ethylphenyl)ethyl]pyridine
2-(p-ethoxyphenyl)-5-[2'-(p'-propylphenyl)ethyl]pyridine
2-(p-ethoxyphenyl)-5-[2'-(p'-butylphenyl)ethyl]pyridine
2-(p-ethoxyphenyl)-5-[2'-(p'-pentylphenyl)ethyl]pyridine
2-(p-ethoxyphenyl)-5-[2'-(p'-hexylphenyl)ethyl]pyridine
2-(p-propyloxyphenyl)-5-[2'-(p'-ethylphenyl)ethyl]pyridine
2-(p-propyloxyphenyl)-5-[2'-(p'-propylphenyl)ethyl]pyridine
2-(p-propyloxyphenyl)-5-[2'-(p'-butylphenyl)ethyl]pyridine
2-(p-propyloxyphenyl)-5-[2'-(p'-pentylphenyl)ethyl]pyridine
2-(p-propyloxyphenyl)-5-[2'-(p'-hexylphenyl)ethyl]pyridine
2-(p-butyloxyphenyl)-5-[2'-(p'-ethylphenyl)ethyl]pyridine
2-(p-butyloxyphenyl)-5-[2'-(p'-propylphenyl)ethyl]pyridine
2-(p-butyloxyphenyl)-5-[2'-(p'-butylphenyl)ethyl]pyridine
2-(p-butyloxyphenyl)-5-[2'-(p'-pentylphenyl)ethyl]pyridine
2-(p-butyloxyphenyl)-5-[2'-(p'-hexylphenyl)ethyl]pyridine
2-(p-pentyloxyphenyl)-5-[2'-(p'-ethylphenyl)ethyl]pyridine
2-(p-pentyloxyphenyl)-5-[2'-(p'-propylphenyl)ethyl]pyridine
2-(p-pentyloxyphenyl)-5-[2'-(p'-butylphenyl)ethyl]pyridine
2-(p-pentyloxyphenyl)-5-[2'-(p'-pentylphenyl)ethyl]pyridine
2-(p-pentyloxyphenyl)-5-[2'-(p'-hexylphenyl)ethyl]pyridine
2-(p-hexyloxyphenyl)-5-[2'-(p'-ethylphenyl)ethyl]pyridine
2-(p-hexyloxyphenyl)-5-[2'-(p'-propylphenyl)ethyl]pyridine
2-(p-hexyloxyphenyl)-5-[2'-(p'-butylphenyl)ethyl]pyridine
2-(p-hexyloxyphenyl)-5-[2'-(p'-pentylphenyl)ethyl]pyridine
2-(p-hexyloxyphenyl)-5-[2'-(p'-hexylphenyl)ethyl]pyridine
2-(p-ethylphenyl)-5-[2'-(p'-ethoxyphenyl)ethyl]pyridine
2-(p-ethylphenyl)-5-[2'-(p'-propyloxyphenyl)ethyl]pyridine
2-(p-ethylphenyl)-5-[2'-(p'-butyloxyphenyl)ethyl]pyridine
2-(p-ethylphenyl)-5-[2'-(p'-pentyloxyphenyl)ethyl]pyridine
2-(p-ethylphenyl)-5-[2'-(p'-hexyloxyphenyl)ethyl]pyridine
2-(p-propylphenyl)-5-[2'-(p'-ethoxyphenyl)ethyl]pyridine
2-(p-propylphenyl)-5-[2'-(p'-propyloxyphenyl)ethyl]pyridine
2-(p-propylphenyl)-5-[2'-(p'-butyloxyphenyl)ethyl]pyridine
2-(p-propylphenyl)-5-[2'-(p'-pentyloxyphenyl)ethyl]pyridine
2-(p-propylphenyl)-5-[2'-(p'-hexyloxyphenyl)ethyl]pyridine
2-(p-butylphenyl)-5-[2'-(p'-ethoxyphenyl)ethyl]pyridine
2-(p-butylphenyl)-5-[2'-(p'-propyloxyphenyl)ethyl]pyridine
2-(p-butylphenyl)-5-[2'-(p'-butyloxyphenyl)ethyl]pyridine
2-(p-butylphenyl)-5-[2'-(p'-pentyloxyphenyl)ethyl]pyridine

C→I 147° C., I→S 146.8° C.

2-(p-butylphenyl)-5-[2'-(p'-hexyloxyphenyl)ethyl]pyridine 2-(p-pentylphenyl)-5-[2'-(p'-ethoxyphenyl)ethyl]pyridine 2-(p-pentylphenyl)-5-[2'-(p'-propyloxyphenyl)ethyl]pyridine 2-(p-pentylphenyl)-5-[2'-(p'-butyloxyphenyl)ethyl]pyridine 2-(p-pentylphenyl)-5-[2'-(p'-pentyloxyphenyl)ethyl]pyridine

C→I 151° C.

2-(p-pentylphenyl)-5-[2'-(p'-hexyloxyphenyl)ethyl]pyridine 2-(p-hexylphenyl)-5-[2'-(p'-ethoxyphenyl)ethyl]pyridine 2-(p-hexylphenyl)-5-[2'-(p'-propyloxyphenyl)ethyl]pyridine 2-(p-hexylphenyl)-5-[2'-(p'-butyloxyphenyl)ethyl]pyridine 2-(p-hexylphenyl)-5-[2'-(p'-pentyloxyphenyl)ethyl]pyridine 2-(p-hexylphenyl)-5-[2'-(p'-hexyloxyphenyl)ethyl]pyridine

EXAMPLE 5

75g of bromobenzene was acylated with 101.3g of (trans-4-propyl) cyclohexylacetylchloride under the same condition as in Example 2 to yield 85.3 of p-[(trans-4-propyl)cyclohexylacetyl]bromobenzene. This compound was reduced under the same condition as in Example 2 to yield 25g of p-[2-(trans-4'-propylcyclohexyl)ethyl]bromobenzene. Then this compound was processed with n-butyllithium under the same condition as in Example 2 to yield p-[2-(trans-4'-propylcyclohexyl)ethyl]phenyllithium. The solution including 14.2g of the resulting compound and 5.1g of pyridine was reacted with 7.75g of 1-bromopropane with chilling and stirring. After the completion of the reaction, the resulting composition was hydrolyzed by adding 200ml of water and the ether layer was washed with water several times. The ether layer was separated and allowed to stand for several hours to obtain the crystals. These crystals were filtered and repeatedly recrystallized from methanol to yield 4.8g of 2-{p-[2'-(trans-4"-propylcyclohexyl)ethyl]phenyl}-5-propylpyridine.

The phase transition temperature of this compound is as below:

C→N 81.2° C., N→I 149° C.

The following are further examples of the compounds in accordance with this embodiment of the invention which may be prepared following the procedure of Example 5:

2-p-[2'-(trans-4"-ethylcyclohexyl)ethyl]phenyl-5-butylpyridine 2-p-[2'-(trans-4"-ethylcyclohexyl)ethyl]phenyl-5-pentylpyridine 2-p-[2'-(trans-4"-ethylcyclohexyl)ethyl]phenyl-5-hexylpyridine 2-p-[2'-(trans-4"-ethylcyclohexy)ethyl]phenyl-5-heptylpyridine 2-p-[2'-(trans-4"-ethylcyclohexyl)ethyl]phenyl-5-octylpyridine 2-p-[2'-(trans-4"-propylcyclohexyl)ethyl]phenyl-5-butylpyridine

C→N 87.6° C., N→I 142.5° C.

2-p-[2'-(trans-4"'-propylcyclohexyl)ethyl]phenyl-5-pentylpyridine

C→N 93.4° C., N→I 156.2° C.

2-p-[2'-(trans-4"-propylcyclohexyl)ethyl]phenyl-5-hexylpyridine 2-p-[2'-(trans-4"-propylcyclohexyl)ethyl]phenyl-5-heptylpyridine 2-p-[2'-(trans-4"-propylcyclohexyl)ethyl]phenyl-5-octylpyridine -butylcyclohexyl)ethyl]phenyl-5-ethylpyridine 2-p-[2'-(trans-4"-butylcyclohexyl)ethyl]phenyl-5-propylpyridine 2-p-[2'-(trans-4"-butylcyclohexyl)ethyl]phenyl-5-butylpyridine 2-p-[2'-(trans-4"-butylcyclohexyl)ethyl]phenyl-5-pentylpyridine

C→N 102° C., N→I 137° C.

2-p-[2'-(trans-4"-butylcyclohexyl)ethyl]phenyl-5-hexylpyridine 2-p-[2'-(trans-4"-butylcyclohexyl)ethyl]phenyl-5-heptylpyridine 2-p-[2'-(trans-4"-butylcyclohexyl)ethyl]phenyl-5-octylpyridine

C→S 79° C., S→N 148° C., N→I 153° C.

2-p-[2'-(trans-4"-pentylcyclohexyl)ethyl]phenyl-5-ethylpyridine 2-p-[2'-(trans-4"-pentylcyclohexyl)ethyl]phenyl-5-propylpyridine 2-p-[2'-(trans-4"-pentylcyclohexyl)ethyl]phenyl-5-butylpyridine 2-p-[2'-(trans-4"-pentylcyclohexyl)ethyl]phenyl-5-pentylpyridine

C→S 98.5° C., S→N 140.5° C., N→I 146° C.

2-p-[2'-(trans-4"-pentylcyclohexyl)ethyl]phenyl-5-hexylpyridine 2-p-[2'-(trans-4"-pentylcyclohexyl)ethyl]phenyl-5-heptylpyridine 2-p-[2'-(trans-4"-pentylcyclohexyl)ethyl]phenyl-5-octylpyridine 2-p-[2'-(trans-4"-hexylcyclohexyl)ethyl]phenyl-5-ethylpyridine 2-p-[2'-(trans-4"-hexylcyclohexyl)ethyl]phenyl-5-propylpyridine 2-p-[2'-(trans-4"-hexylcyclohexyl)ethyl]phenyl-5-butylpyridine 2-p-[2'-(trans-4"-hexylcyclohexyl)ethyl]phenyl-5-pentylpyridine 2-p-[2'-(trans-4"-hexylcyclohexyl)ethyl]phenyl-5-hexylpyridine 2-p-[2'-(trans-4"-hexylcyclohexyl)ethyl]phenyl-5-heptylpyridine 2-p-[2'-(trans-4"-hexylcyclohexyl)ethyl]phenyl-5-octylpyridine 2-p-[2'-(trans-4"-heptylcyclohexyl)ethyl]phenyl-5-ethylpyridine 2-p-[2'-(trans-4"-heptylcyclohexyl)ethyl]phenyl-5-propylpyridine 2-p-[2'-(trans-4"-heptylcyclohexyl)ethyl]phenyl-5-butylpyridine 2-p-[2'-(trans-4''-heptylcyclohexyl)ethyl]phenyl-5-pentylpyridine
2-p-[2'-(trans-4''-heptylcyclohexyl)ethyl]phenyl-5-hexylpyridine
2-p-[2'-(trans-4''-heptylcyclohexyl)ethyl]phenyl-5-heptylpyridine
2-p-[2'-(trans-4''-heptylcyclohexyl)ethyl]phenyl-5-octylpyridine
2-p-[2'-(trans-4''-octylcyclohexyl)ethyl]phenyl-5-ethylpyridine
2-p-[2'-(trans-4''-octylcyclohexyl)ethyl]phenyl-5-propylpyridine
2-p-[2'-(trans-4''-octylcyclohexyl)ethyl]phenyl-5-butylpyridine
2-{p-[2'-(trans-4''-octylcyclohexyl)ethyl]phenyl}-5-pentylpyridine
2-{p-[2'-(trans-4''-octylcyclohexyl)ethyl]phenyl}-5-hexylpyridine
2-{p-[2'-(trans-4''-octylcyclohexyl)ethyl]phenyl}-5-heptylpyridine
2-{p-[2'-(trans-4''-octylcyclohexyl)ethyl]phenyl}-5-octylpyridine
2-{p-[2'-(p'-ethylphenyl)ethyl]phenyl}-5-ethylpyridine
2-{p-[2'-(p'-ethoxyphenyl)ethyl]phenyl}-5-ethylpyridine
2-{p-[2'-(p'-ethylphenyl)ethyl]phenyl}-5-propylpyridine
2-{p-[2'-(p'-ethoxyphenyl)ethyl]phenyl}-5-propylpyridine
2-{p-[2'-(p'-ethylphenyl)ethyl]phenyl}-5-butylpyridine
2-{p-[2'-(p'-ethoxyphenyl)ethyl]phenyl}-5-butylpyridine
2-{p-[2'-(p'-ethylphenyl)ethyl]phenyl}-5-pentylpyridine
2-{p-[2'-(p'-ethoxyphenyl)ethyl]phenyl}-5-pentylpyridine
2-{p-[2'-(p'-ethylphenyl)ethyl]phenyl}-5-hexylpyridine
2-{p-[2'-(p'-ethoxyphenyl)ethyl]phenyl}-5-hexylpyridine
2-{p-[2'-(p'-ethylphenyl)ethyl]phenyl}-5-heptylpyridine
2-{p-[2'-(p'-ethoxyphenyl)ethyl]phenyl}-5-heptylpyridine
2-{p-[2'-(p'-ethylphenyl)ethyl]phenyl}-5-octylpyridine
2-{p-[2'-(p'-ethoxyphenyl)ethyl]phenyl}-5-octylpyridine
2-{p-[2'-(p'-propylphenyl)ethyl]phenyl}-5-ethylpyridine
2-{p-[2'-(p'-propyloxyphenyl)ethyl]phenyl}-5-ethylpyridine
2-{p-[2'-(p'-propylphenyl)ethyl]-phenyl}-5-propylpyridine
2-{p-[2'-(p'-propyloxyphenyl)ethyl]phenyl}-5-propylpyridine
2-{p-[2'-(p'-propylphenyl)ethyl]phenyl}-5-butylpyridine
2-{p-[2'-(p'-propyloxyphenyl)ethyl]phenyl}-5-butylpyridine
2-{p-[2'-(p'-propylphenyl)ethyl]phenyl}-5-pentylpyridine
2-{p-[2'-(p'-propyloxyphenyl)ethyl]phenyl}-5-pentylpyridine
2-{p-[2'-(p'-propylphenyl)ethyl]phenyl}-5-hexylpyridine
2-{p-[2'-(p'-propyloxyphenyl)ethyl]phenyl}-5-hexylpyridine
2-{p-[2'-(p'-propylphenyl)ethyl]phenyl}-5-heptylpyridine
2-{p-[2'-(p'-propyloxyphenyl)ethyl]phenyl}-5-heptylpyridine
2-{p-[2'-(p'-propylphenyl)ethyl]phenyl}-5-octylpyridine
2-{p-[2'-(p'-propyloxyphenyl)ethyl]phenyl}-5-octylpyridine
2-{p-[2'-(p'-butylphenyl)ethyl]phenyl}-5-ethylpyridine
2-{p-[2'-(p'-butyloxyphenyl)ethyl]phenyl}-5-ethylpyridine
2-{p-[2'-(p'-butylphenyl)ethyl]phenyl}-5-propylpyridine
2-{p-[2'-(p'-butyloxyphenyl)ethyl]phenyl}-5-propylpyridine
2-{p-[2'-(p'-butylphenyl)ethyl]phenyl}-5-butylpyridine
2-{p-[2'-(p'-butyloxyphenyl)ethyl]phenyl}-5-butylpyridine
2-{p-[2'-(p'-butylphenyl)ethyl]phenyl}-5-pentylpyridine
2-{p-[2'-(p'-butyloxyphenyl)ethyl]phenyl}-5-pentylpyridine
2-{p-[2'-(p'-butylphenyl)ethyl]phenyl}-5-hexylpyridine
2-{p-[2'-(p'-butyloxyphenyl)ethyl]phenyl}-5-hexylpyridine
2-{p-[2'-(p'-butylphenyl)ethyl]phenyl}-5-heptylpyridine
2-{p-[2'-(p'-butyloxyphenyl)ethyl]phenyl}-5-heptylpyridine
2-{p-[2'-(p'-butylphenyl)ethyl]phenyl}-5-octylpyridine
2-{p-[2'-(p'-butyloxyphenyl)ethyl]phenyl}-5-octylpyridine
2-{p-[2'-(p'-pentylphenyl)ethyl]phenyl}-5-ethylpyridine
2-{p-[2'-(p'-pentyloxyphenyl)ethyl]phenyl}-5-ethylpyridine
2-{p-[2'-(p'-pentylphenyl)ethyl]phenyl}-5-propylpyridine
2-{p-[2'-(p'-pentyloxyphenyl)ethyl]phenyl}-5-propylpyridine
2-{p-[2'-(p'-pentylphenyl)ethyl]phenyl}-5-butylpyridine
2-{p-[2'-(p'-pentyloxyphenyl)ethyl]phenyl}-5-butylpyridine
2-{p-[2'-(p'-pentylphenyl)ethyl]phenyl}-5-pentylpyridine

C→S 113° C, S→N 118° C, N→I 120° C.

2-{p-[2'-(p'-pentyloxyphenyl)ethyl]phenyl}-5-pentylpyridine
2-{p-[2'-(p'-pentylphenyl)ethyl]phenyl}-5-hexylpyridine
2-{p-[2'-(p'-pentyloxyphenyl)ethyl]phenyl}-5-hexylpyridine
2-{p-[2'-(p'-pentylphenyl)ethyl]phenyl}-5-heptylpyridine
2-{p-[2'-(p'-pentyloxyphenyl)ethyl]phenyl}-5-heptylpyridine
2-{p-[2'-(p'-pentylphenyl)ethyl]phenyl}-5-octylpyridine
2-{p-[2'-(p'-pentyloxyphenyl)ethyl]phenyl}-5-octylpyridine
2-{p-[2'-(p'-hexylphenyl)ethyl]phenyl}-5-ethylpyridine
2-{p-[2'-(p'-hexyloxyphenyl)ethyl]phenyl}-5-ethylpyridine
2-{p-[2'-(p'-hexylphenyl)ethyl]phenyl}-5-propylpyridine
2-{p-[2'-(p'-hexyloxyphenyl)ethyl]phenyl}-5-propylpyridine 2-{p-[2'-(p'-hexylphenyl)ethyl]phenyl}-5-butylpyridine
2-{p-[2'-(p'-hexyloxyphenyl)ethyl]phenyl}-5-butylpyridine
2-{p-[2'-(p'-hexylphenyl)ethyl]phenyl}-5-pentylpyridine
2-{p-[2'-(p'-hexyloxyphenyl)ethyl]phenyl}-5-pentylpyridine
2-{p-[2'-(p'-hexylphenyl)ethyl]phenyl}-5-hexylpyridine
2-{p-[2'-(p'-hexyloxyphenyl)ethyl]phenyl}-5-hexylpyridine
2-{p-[2'-(p'-hexylphenyl)ethyl]phenyl}-5-heptylpyridine
2-{p-[2'-(p'-hexyloxyphenyl)ethyl]phenyl}-5-heptylpyridine
2-{p-[2'-(p'-hexylphenyl)ethyl]phenyl}-5-octylpyridine
2-{p-[2'-(p'-hexyloxyphenyl)ethyl]phenyl}-5-octylpyridine
2-{p-[2'-(p'-heptylphenyl)ethyl]phenyl}-5-ethylpyridine
2-{p-[2'-(p'-heptyloxyphenyl)ethyl]phenyl}-5-ethylpyridine
2-{p-[2'-(p'-heptylphenyl)ethyl]phenyl}-5-propylpyridine
2-{p-[2'-(p'-heptyloxyphenyl)ethyl]phenyl}-5-propylpyridine
2-{p-[2'-(p'-heptylphenyl)ethyl]phenyl}-5-butylpyridine
2-{p-[2'-(p'-heptyloxyphenyl)ethyl]phenyl}-5-butylpyridine
2-{p-[2'-(p'-heptylphenyl)ethyl]phenyl}-5-pentylpyridine
2-{p-[2'-(p'-heptyloxyphenyl)ethyl]phenyl}-5-pentylpyridine
2-{p-[2'-(p'-heptylphenyl)ethyl]phenyl}-5-hexylpyridine
2-{p-[2'-(p'-heptyloxyphenyl)ethyl]phenyl}-5-hexylpyridine
2-{p-[2'-(p'-heptylphenyl)ethyl]phenyl}-5-heptylpyridine
2-{p-[2'-(p'-heptyloxyphenyl)ethyl]phenyl}-5-heptylpyridine
2-{p-[2'-(p'-heptylphenyl)ethyl]phenyl}-5-octylpyridine
2-{p-[2'-(p'-heptyloxyphenyl)ethyl]phenyl}-5-octylpyridine
2-{p-[2'-(p'-octylphenyl)ethyl]phenyl}-5-ethylpyridine
2-{p-[2'-(p'-octyloxyphenyl)ethyl]phenyl}-5-ethylpyridine
2-{p-[2'-(p'-octylphenyl)ethyl]phenyl}-5-propylpyridine
2-{p-[2'-(p'-octyloxyphenyl)ethyl]phenyl}-5-propylpyridine
2-{p-[2'-(p'-octylphenyl)ethyl]phenyl}-5-butylpyridine
2-{p-[2'-(p'-octyloxyphenyl)ethyl]phenyl}-5-butylpyridine
2-{p-[2'-(p'-octylphenyl)ethyl]phenyl}-5-pentylpyridine
2-{p-[2'-(p'-octyloxyphenyl)ethyl]phenyl}-5-pentylpyridine
2-{p-[2'-(p'-octylphenyl)ethyl]phenyl}-5-hexylpyridine
2-{p-[2'-(p'-octyloxyphenyl)ethyl]phenyl}-5-hexylpyridine
2-{p-[2'-(p'-octylphenyl)ethyl]phenyl}-5-heptylpyridine
2-{p-[2'-(p'-octyloxyphenyl)ethyl]phenyl}-5-heptylpyridine
2-{p-[2'-(p'-octylphenyl)ethyl]phenyl}-5-octylpyridine
2-{p-[2'-(p'-octyloxyphenyl)ethyl]phenyl}-5-octylpyridine

EXAMPLE 6

Diethylether including the reaction products of 28.4g of p-[2-(trans-4'-propylcyclohexyl)ethyl]phenyllithium obtained as in Example 5 and 10.2g of dry pyridine was processed first with iron pentacarbonyl and then with methyl iodide as in Embodiment 3. Then the fraction having a boiling point of 245° to 250° C./2mmHg was recrystallized from ethanol to yield 16g of 2-p-[2'-(trans-4"-propylcyclohexyl)ethyl]phenyl-5-acetylpyridine.

This compound was processed with hydroxylamine hydrochloric acid salt, 85% phosphoric acid, polyphosphoric acid and an aqueous solution of sodium hydroxide, respectively and the fraction having a boiling point of 220° to 225° C./2mmHg was obtained to yield 5.7g of 2-{p-[2'-(trans-4"-propylcyclohexylethyl]phenyl}-5-animopyridine.

This compound was then processed with sulfuric acid and water and sodium nitrite to yield 4.5g of 2-{p-[2'-(trans-4"-propylcyclohexyl)ethyl]phenyl}-5-hydroxypyridine.

The resulting compound was reacted with 1.7g of 1-bromoethane to yield 3.5g of 2-{p-[2'-(trans-4"-propylcyclohexyl)ethyl]phenyl}-5-ethoxypyridine.

The phase transition temperature of this compound was as follows:

C→S 120.5° C., S→N 142° C., N→I 157° C.

The following are further examples of the compounds in accordance with this embodiment of the invention which may be prepared following the procedure of Example 6:

2-{p-[2'-(trans-4"-ethylcyclohexyl)ethyl]phenyl}-5-ethoxypyridine
2-{p-[2'-(trans-4"-ethylcyclohexyl)ethyl]phenyl}-5-propyloxypyridine
2-{p-[2'-(trans-4"-ethylcyclohexyl)ethyl]phenyl}-5-butyloxypyridine
2-{p-[2'-(trans-4"-ethylcyclohexyl)ethyl]phenyl}-5-pentyloxypyridine
2-{p-[2'-(trans-4"-ethylcyclohexyl)ethyl]phenyl}-5-hexyloxypyridine
2-{p-[2'-(trans-4"-ethylcyclohexyl)ethyl]phenyl}-5-heptyloxypyridine
2-{p-[2'-(trans-4"-ethylcyclohexyl)ethyl]phenyl}-5-octyloxypyridine
2-{p-[2'-(trans-4"-propylcycloehxyl)ethyl]phenyl}-5-propyloxypyridine
2-{p-[2'-(trans-4"-propylcyclohexyl)ethyl]phenyl}-5-butyloxypypyridine

C→S 111° C., S→N 135° C., N→I 142° C.

2-{p-[2'-(trans-4"-propylcyclohexyl)ethyl]phenyl}-5-pentyloxypyridine
2-{p-[2'-(trans-4"-propylcyclohexyl)ethyl]phenyl}-5-hexyloxypyridine
2-{p-[2'-(trans-4"-propylcyclohexyl)ethyl]phenyl}-5-heptyloxypyridine
2-{p-[2'-(trans-4"-propylcyclohexyl)ethyl]phenyl}-5-octyloxypyridine
2-{p-[2'-(trans-4"-butylcyclohexyl)ethyl]phenyl}-5-ethoxypyridine 2-{p-[2'-(trans-4"-butycyclohexyl)ethyl]phenyl}-5-propyloxypyridine
2-{p-[2'-(trans-4"-butycyclohexyl)ethyl]phenyl}-5-butyloxypyridine
2-{p-[2'-(trans-4"-butycyclohexyl)ethyl]phenyl}-5-pentyloxypyridine
2-{p-[2'-(trans-4"-butycyclohexyl)ethyl]phenyl}-5-hexyloxypyridine
2-{p-[2'-(trans-4"-butycyclohexyl)ethyl]phenyl}-5-heptyloxypyridine
2-{p-[2'-(trans-4"-butycyclohexyl)ethyl]phenyl}-5-octyloxypyridine
2-{p-[2'-(trans-4"-pentylcyclohexyl)ethyl]phenyl}-5-ethoxypyridine
2-{p-[2'-(trans-4"-pentylcyclohexyl)ethyl]phenyl}-5-propyloxypyridine
2-{p-[2'-(trans-4"-pentylcyclohexyl)ethyl]phenyl}-5-butyloxypyridine
2-{p-[2'-(trans-4"-pentylcyclohexyl)ethyl]phenyl}-5-pentyloxypyridine
2-{p-[2'-(trans-4"-pentylcyclohexyl)ethyl]phenyl}-5-hexyloxypyridine
2-{p-[2'-(trans-4"-pentylcyclohexyl)ethyl]phenyl}-5-heptyloxypyridine
2-{p-[2'-(trans-4"-pentylcyclohexyl)ethyl]phenyl}-5-octyloxypyridine
2-{p-[2'-(trans-4"-hexylcyclohexyl)ethyl]phenyl}-5-ethoxypyridine
2-{p-[2'-(trans-4"-hexylcyclohexyl)ethyl]phenyl}-5-propyloxypyridine
2-{p-[2'-(trans-4"-hexylcyclohexyl)ethyl]phenyl}-5-butyloxypyridine
2-{p-[2'-(trans-4"-hexylcyclohexyl)ethyl]phenyl}-5-pentyloxypyridine
2-{p-[2'-(trans-4"-hexylcyclohexyl)ethyl]phenyl}-5-hexyloxypyridine
2-{p-[2'-(trans-4"-hexylcyclohexyl)ethyl]phenyl}-5-heptyloxypyridine
2-{p-[2'-(trans-4"-hexylcyclohexyl)ethyl]phenyl}-5-octyloxypyridine
2-{p-[2'-(trans-4"-heptylcyclohexyl)ethyl]phenyl}-5-ethoxypyridine
2-{p-[2'-(trans-4"-heptylcyclohexyl)ethyl]phenyl}-5-propyloxypyridine
2-{p-[2'-(trans-4"-heptylcyclohexyl)ethyl]phenyl}-5-butyloxypyridine
2-{p-[2'-(trans-4"-heptylcyclohexyl)ethyl]phenyl}-5-pentyloxypyridine
2-{p-[2'-(trans-4"-heptylcyclohexyl)ethyl]phenyl}-5-hexyloxypyridine
2-{p-[2'-(trans-4"-heptylcyclohexyl)ethyl]phenyl}-5-heptyloxypyridine
2-{p-[2'-(trans-4"-heptylcyclohexyl)ethyl]phenyl}-5-octyloxypyridine
2-{p-[2'-(trans-4"-octylcyclohexyl)ethyl]phenyl}-5-ethoxypyridine
2-{p-[2'-(trans-4"-octylcyclohexyl)ethyl]phenyl}-5-propyloxypyridine
2-{p-[2'-(trans-4"-octylcyclohexyl)ethyl]phenyl}-5-butyloxypyridine
2-{p-[2'-(trans-4"-octylcyclohexyl)ethyl]phenyl}-5-pentyloxypyridine
2-{p-[2'-(trans-4"-octylcyclohexyl)ethyl]phenyl}-5-hexyloxypyridine
2-{p-[2'-(trans-4"-octylcyclohexyl)ethyl]phenyl}-5-heptyloxypyridine
2-{p-[2-(trans-4"-octylcyclohexyl)ethyl]phenyl}-5-octyloxypyridine
2-{p-[2'-(p'-ethylphenyl)ethyl]phenyl}-5-ethoxypyridine
2-{p-[2'-(p'-ethylphenyl)ethyl]phenyl}-5-propyloxypyridine
2-{p-[2'-(p'-ethylphenyl)ethyl]phenyl}-5-butyloxypyridine
2-{p-[2'-(p'-ethylphenyl)ethyl]phenyl}-5-pentyloxypyridine
2-{p-[2'-(p'-ethylphenyl)ethyl]phenyl}-5-hexyloxypyridine
2-{p-[2'-(p'-ethylphenyl)ethyl]phenyl}-5-heptyloxypyridine
2-{p-[2'-(p'-ethylphenyl)ethyl]phenyl}-5-octyloxypyridine
2-{p-[2'-(p'-propylphenyl)ethyl]phenyl}-5-ethoxypyridine
2-{p-[2'-(p'-propylphenyl)ethyl]phenyl}-5-propyloxypyridine
2-{p-[2'-(p'-propylphenyl)ethyl]phenyl}-5-butyloxypyridine
2-{p-[2'-(p'-propylphenyl)ethyl]phenyl}-5-pentyloxypyridine
2-{p-[2'-(p'-propylphenyl)ethyl]phenyl}-5-hexyloxypyridine
2-{p-[2'-(p'-propylphenyl)ethyl]phenyl}-5-heptyloxypyridine
2-{p-[2'-(p'-propylphenyl)ethyl]phenyl}-5-octyloxypyridine
2-{p-[2'-(p'-butylphenyl)ethyl]phenyl}-5-ethoxypyridine
2-{p-[2'-(p'-butylphenyl)ethyl]phenyl}-5-propyloxypyridine
2-{p-[2'-(p'-butylphenyl)ethyl]phenyl}-5-butyloxypyridine
2-{p-[2'-(p'-butylphenyl)ethyl]phenyl}-5-pentyloxypyridine
2-{p-[2'-(p'-butylphenyl)ethyl]phenyl}-5-hexyloxypyridine
2-{p-[2'-(p'-butylphenyl)ethyl]phenyl}-5-heptyloxypyridine
2-{p-[2'-(p'-butylphenyl)ethyl]phenyl}-5-octyloxypyridine
2-{p-[2'-(p'-pentylphenyl)ethyl]phenyl}-5-ethoxypyridine
2-{p-[2'-(p'-pentylphenyl)ethyl]phenyl}-5-propyloxypyridine
2-{p-[2'-(p'-pentylphenyl)ethyl]phenyl}-5-butyloxypyridine
2-{p-[2'-(p'-pentylphenyl)ethyl]phenyl}-5-pentyloxypyridine
2-{p-[2'-(p'-pentylphenyl)ethyl]phenyl}-5-hexyloxypyridine
2-{p-[2'-(p'-pentylphenyl)ethyl]phenyl}-5-heptyloxypyridine
2-{p-[2'-(p'-pentylphenyl)ethyl]phenyl}-5-octyloxypyridine
2-{p-[2'-(p'-hexylphenyl)ethyl]phenyl}-5-ethoxypyridine
2-{p-[2'-(p'-hexylphenyl)ethyl]phenyl}-5-propyloxypyridine
2-{p-[2'-(p'-hexylphenyl)ethyl]phenyl}-5-butyloxypyridine
2-{p-[2'-(p'-hexylphenyl)ethyl]phenyl}-5-pentyloxypyridine
2-{p-[2'-(p'-hexylphenyl)ethyl]phenyl}-5-hexyloxypyridine
2-{p-[2'-(p'-hexylphenyl)ethyl]phenyl}-5-heptyloxypyridine 2-{p-[2'-(p'-hexylphenyl)ethyl]phenyl}-5-octyloxypyridine 2-{p-[2'-(p'-heptylphenyl)ethyl]phenyl}-5-ethoxypyridine 2-{p-[2'-(p'-heptylphenyl)ethyl]phenyl}-5-propyloxypyridine 2-{p-[2'-(p'-heptylphenyl)ethyl]phenyl}-5-butyloxypyridine 2-{p-[2'-(p'-heptylphenyl)ethyl]phenyl}-5-pentyloxypyridine 2-{p-[2'-(p'-heptylphenyl)ethyl]phenyl}-5-hexyloxypyridine 2-{p-[2'-(p'-heptylphenyl)ethyl]phenyl}-5-heptyloxypyridine 2-{p-[2'-(p'-heptylphenyl)ethyl]phenyl}-5-octyloxypyridine 2-{p-[2'-(p'-octylphenyl)ethyl]phenyl}-5-ethoxypyridine 2-{p-[2'-(p'-octylphenyl)ethyl]phenyl}-5-propyloxypyridine 2-{p-[2'-(p'-octylphenyl)ethyl]phenyl}-5-butyloxypyridine 2-{p-[2'-(p'-octylphenyl)ethyl]phenyl}-5-pentyloxypyridine 2-{p-[2'-(p'-octylphenyl)ethyl]phenyl}-5-hexyloxypyridine 2-{p-[2'-(p'-octylphenyl)ethyl]phenyl}-5-heptyloxypyridine 2-{p-[2'-(p'-octylphenyl)ethyl]phenyl}-5-octyloxypyridine

EXAMPLE 7

Diethylether solution including the reaction products of 28 g of p-[2-(trans-4"-propylcyclohexyl)ethyl]phenyllithium and 10.2 g of dry pyridine was chilled to −20° C. and the solution of 24 g of bromine and 200 ml of dry tetrahydrofuran was added drop-wise with stirring. Then the temperature of the solution was raised to room temperature and stirring was continued for 2 hours. After completion of the reaction, 200 ml of water was added and the ether layer was separated and washed with water several times. Ether was removed by distillation and the residue was recrystallized with methanol. 9.3 g of the mixture including about 60% of the yielded 2-{p-[2'-trans-4"-propylcyclohexyl)ethyl]phenyl}-5-bromopyridine and 1.75 g of cuprous cyanide was heated to 180° C. for 5 hours in 80 ml of N-methylpyrrolidone. The resulting mixture was added to the solution of 6.8 g of ferric chloride, 15 ml of hydrochloric acid and 80 ml of water and the mixture was heated to 60° C. for 30 minutes and stirred.

After chilling the resulting mixture, the oil layer was extracted with chloroform and washed with 5N hydrochloric acid and water several times and then chloroform was removed by distillation. The residue was isolated by column chromatography on silica gel, first with hexane and then with benzene and recrystallized from ethanol to yield 1.8 g of 2-{p-[2'-(trans-4"-propylcyclohexyl)ethyl]phenyl}-5-cyanopyridine.

The phase transition temperature of this compound is as below:

C→S 96.5° C., S→N 163.5° C., N→I 176.5° C.

The following are further examples of the compounds in accordance with this embodiment of the invention which may be prepared following the procedure of Example 7:

2-{p-[2'-(trans-4"-ethylcyclohexyl)ethyl]phenyl}-5-cyanopyridine

2-{p-[2'-(trans-4"-butycyclohexyl)ethyl]phenyl}-5-cyanopyridine

C→S 130.5° C., S→N 165° C., N→I 168° C.

2-{p-[2'-(trans-4"-pentycyclohexyl)ethyl]phenyl}-5-cyanopyridine

C→S 96° C., S→S 165° C., N→I 172° C.

2-{p-[2'-(trans-4"-hexycyclohexyl)ethyl]phenyl}-5-cyanopyridine

2-{p-[2'-(trans-4"-heptylcyclohexyl)ethyl]phenyl}-5-cyanopyridine

2-{p-[2'-(trans-4"-octycyclohexyl)ethyl]phenyl}-5-cyanopyridine

2-{p-[2'-(p'-4"'-ethylphenyl)ethyl]phenyl}-5-cyanopyridine

2-{p-[2'-(p'-propyphenyl)ethyl]phenyl}-5-cyanopyridine

2-{p-[2'-(p'-butylphenyl)ethyl]phenyl}-5-cyanopyridine

2-{p-[2'-(p'-pentylphenyl)ethyl]phenyl}-5-cyanopyridine

2-{p-[2'-(p'-hexylphenyl)ethyl]phenyl}-5-cyanopyridine

2-{p-[2'-(p'-heptylphenyl)ethyl]phenyl}-5-cyanopyridine

2-{p-[2'-(p'-octylphenyl)ethyl]phenyl}-5-cyanopyridine

2-{p-[2'-(p'-ethoxyphenyl)ethyl]phenyl}-5-cyanopyridine

2-{p-[2'-(p'-propyloxphenyl)ethl]phenyl}-5-cyanopyridine

2-{p-[2'-(p'-butyloxyphenyl)ethyl]phenyl}-5-cyanopyridine

2-{p-[2'-(p'-pentyloxyphenyl)ethyl]phenyl}-5-cyanopyridine

2-{p-[2'-(p'-hexyloxyphenyl)ethyl]phenyl}-5-cyanopyridine

2-{p-[2'-(p'-heptyloxyphenyl)ethyl]phenyl}-5-cyanopyridine

2-{p-[2'-(p'-octyloxyphenyl)ethyl]phenyl}-5-cyanopyridine

EXAMPLE 8

Following the same procedures as in Example 7, 157 g of bromobenzene was processed first with n-butyllithium, then with pyridine and with 2-(trans-4'-propylcyclohexyl)-1-bromoethane, respectively to yield 49 g of 2-phenyl-5-[2'-(trans-4"-propylcyclohexyl)ethyl]pyridine. 16.6 g of the 2-phenyl-5-[2"'-(trans-4"-propylcyclohexyl)ethyl]pyridine was mixed with 7.8 g of silver sulfate and 60 ml of 98% sulfuric acid. To this mixture, 8 g of bromine was added drop-wise with stirring which was continued for 4 hours thereafter.

After completion of the reaction, the precipitate was removed by filtration and the filtrate was diluted by adding 60 ml of water. Then a small amount of sodium sulfate was added and extracted with chloroform. After fully washing the chloroform layer, the chloroform was removed by distillation. The residue was distilled under reduced pressure and the fraction having a boiling point of 140° to 145° C./2mmHg was extracted and recrystallized from ethanol. 4.5 g of the resulting 2-(p-bromophenyl)-5-[2'-(trans-4"-propylcyclohexyl)ethyl]-pyridine was processed with cuprous cyanide and N-methylpyrrolidone as in Example 7 to yield 1.5 g of 2-(p-cyanophenyl)-5-[2-(trans-4'1-propylcyclohexyl)ethyl]pyridine.

The phase transition temperature of this compound was as follows:

C→S 145° C., S→I 170.5° C.

The following are other examples of the compounds in accordance with this embodiment of the invention which may be preferred following the procedures of Example 8:

2-(p-cyanophenyl)-5-[2'-(trans-4"-ethylcyclohexyl)ethyl]pyridine
2-(p-cyanophenyl)-5-[2'-(trans-4"-butylcyclohexyl)ethyl]pyridine
2-(p-cyanophenyl)-5-[2'-(trans-4"-pentylcyclohexyl)ethyl]pyridine
2-(p-cyanophenyl)-5-[2'-(trans-4"-hexylcyclohexyl)ethyl]pyridine
2-(p-cyanophenyl)-5-[2'-(trans-4"-heptycyclohexyl)ethyl]pyridine
2-(p-cyanophenyl)-5-[2'-(trans-4"-octylcyclohexyl)ethyl]pyridine
2-(p-cyanophenyl)-5-[2'-(p'-ethylphenyl)ethyl]pyridine
2-(p-cyanophenyl)-5-[2'-(p'-propylphenyl)ethyl]pyridine
2-(p-cyanophenyl)-5-[2'-(p'-butylphenyl)ethyl]pyridine
2-(p-cyanophenyl)-5-[2'-(p'-pentylphenyl)ethyl]pyridine
2-(p-cyanophenyl)-5-[2'-(p'-hexylphenyl)ethyl]pyridine
2-(p-cyanophenyl)-5-[2'-(p'-heptylphenyl)ethyl]pyridine
2-(p-cyanophenyl)-5-[2'-(p'-octyphenyl)ethyl]pyridine
2-(p-cyanophenyl)-5-[2'-(p'-ethoxyphenyl)ethyl]pyridine
2-(p-cyanophenyl)-5-[2'-(p'-propyloxyphenyl)ethyl]pyridine
2-(p-cyanophenyl)-5-[2'-(p'-butyloxyphenyl)ethyl]pyridine
2-(p-cyanophenyl)-5-[2'-(p'-pentyloxyphenyl)ethyl]pyridine
2-(p-cyanophenyl)-5-[2'-(p'-hexyloxyphenyl)ethyl]pyridine
2-(p-cyanophenyl)-5-[2'-(p'-heptyloxyphenyl)ethyl]pyridine
2-(p-cyanophenyl)-5-[2'-(p'-octyloxyphenyl)ethyl]pyridine Particularly desirable liquid crystal compositions showing the usefulness of the compounds in accordance with the present invention are described below. The 2-phenylpyridine derivatives represented by the general formula:

wherein, when Y is R—, Z is one of R—, RO—,

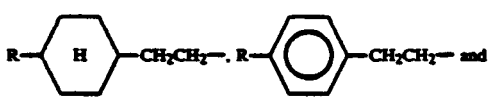

-continued

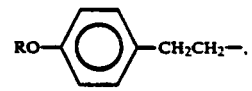

and when Y is RO—, Z is one of straight chain pentyl,

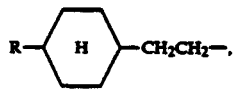

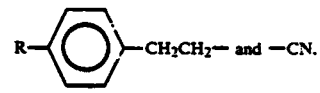

and when Y is one of

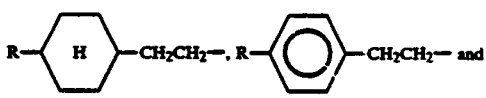

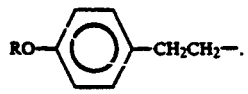

Z is one of R—, RO— and —CN, and when Y is —CN, Z is one of RO—,

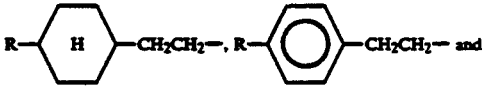

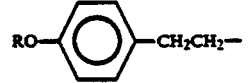

and R is straight chain alkyl having from 1 to 12 carbon atoms; are mixed with the conventional nematic liquid crystal compositions of Nn (nematic with negative dielectric anisotropy) liquid crystal compounds and Np (nematic with positive dielectric anistropy) liquid crystal compounds in order to improve the steepness and the response speed of the compounds. When the 2-phenylpyridine compounds of the invention are included in an amount less than 2 wt %, the effects thereof are not fully achieved. The greater the concentration of the 2-phenylpyridine the better. However, if the concentration is more than 80 wt %, such a composition is far from the eutetic composition and the effect of freezing point depression effect is lost, and consequently deposition occurs at low temperatures. Accordingly, the suitable concentration of PRD of this invention is between aboue 2 and 80 wt %.

It is sometimes desirable to add the liquid crystal compounds having positive dielectric anisotropy in order to adjust the driving voltage appropriately. As suitable Np liquid crystal compounds, the following compounds represented by the general formulae B (hereinafter referred to as "compound B") are recommended:

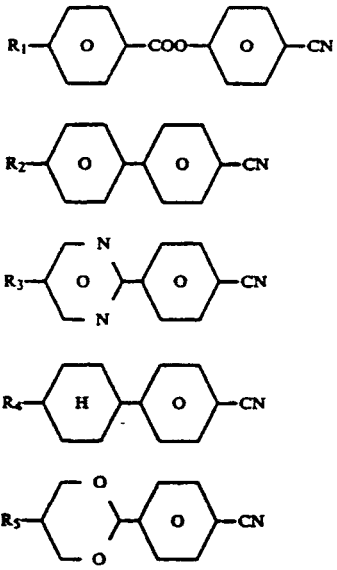

wherein $R_1$ is a straight chain alkyl group having from 1 to 10 carbon atoms and $R_2$, $R_3$, $R_4$ and $R_5$ are straight chain alkyl groups having from 1 to 12 carbon atoms.

The above compounds B are Np liquid crystal compounds which effect the lowering of the threshold voltage depending on the concentration. If the threshold voltage is low, the maximum rate output voltage of the driver circuit of the liquid crystal becomes proportionally low, thereby allowing use of a low-cost integrated circuit, which is very advantageous. However, if the compounds B are present in too high a concentration, undesirable effects may be presented, such that other electro-optical characteristics such as steepness are deteriorated, the liquid crystal temperature range is narrowed and so on. Accordingly, the concentration of compounds B is preferred to be small, suitably between about 2 and 80 wt %.

It is also sometimes desirable to add compounds represented by the general formulae indicated by C (hereinafter referred to as "Compounds C") so that the composition presents a wide nematic liquid crystal temperature range:

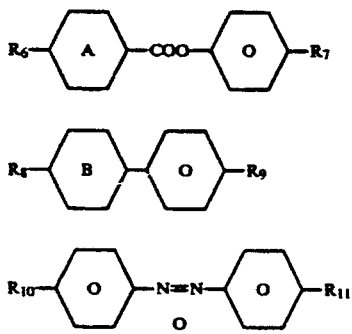

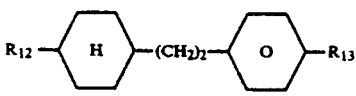

wherein $R_6$ is a straight chain alkyl group having from 1 to 10 carbon atoms, a straigh chain alkoxy group having from 1 to 10 carbon atoms or a straight chain acyoxy group having from 1 to 10 carbon atoms, $R_7$ is a straight chain alkyl group having from 1 to 10 carbon atoms or a straight chain alkoxy group having from 1 to 10 carbon atoms, $R_8$ is a straight chain alkyl group having from 1 to 10 carbon atoms, $R_9$ is a straigh chain alkyl group having from 1 to 15 carbon atoms or a straight chain alkoxy group having from 1 to 15 carbon atoms, $R_{10}$ is a straight chain alkyl group having from 1 to 8 carbon atoms or a straight chain alkoxy group having from 1 to 11 carbon atoms, $R_{11}$ and $R_{12}$ are straight chain alkyl groups having from 1 to 10 carbon atoms, $R_{13}$ is a staight chain alkyl group having from 1 to 10 carbon atoms or a straight chain alkoxy group having from 1 to 10 carbon atoms,

is 1,4-di-substituted cyclohexane or 1,4-di-substituted benzene and

is trans-1,4-di-substituted cyclohexane, trans-2,5-di-substituted 1,3-dioxane or 2,5-di-substituted pyrimidine.

The compounds C are important in respect of not presenting the complete soluble solid with Compounds A. Compounds C present the eutetic producing type freezing with PRD, the composition presents the nematic liquid crystal phase without freezing even at much lower temperature than the melting point of other ingredients.

Furthermore, the clear point of compounds C is between about room temperature to 60° C. Thus, adding Compounds C does not lower the clear point of the nematic liquid crystal composition.

The above two effects of Compounds C, result in the nematic liquid crystal temperature range being expanded to both lower and higher temperatures. If the liquid crystal composition is to be used in the usual temperature range, for example, between 0° to 40° C., Compounds C are not necessary. However, if the liquid crystal composition is to be used in a wider temperature range, for example, between −20° to 60° C., it is preferable to add compounds C in an amount of at least 2 wt %. If the compounds C are present in the composition in an amount more than 86 wt %, the concentration of the composition is far from the eutetic composition and the freezing point depression effect is no longer present. Accordingly, the suitable concentration of compounds C is between 0 to 86 wt %, and more preferably between about 2 to 86 wt %.

When the liquid crystal composition is to be used in an extremely wide temperature range such as when used in a car, it is desirable to add the compounds represented by the general formulae indicated by D (hereinafter referred to as "Compounds D") in order to widen further the nematic liquid crystal temperature range of the composition:

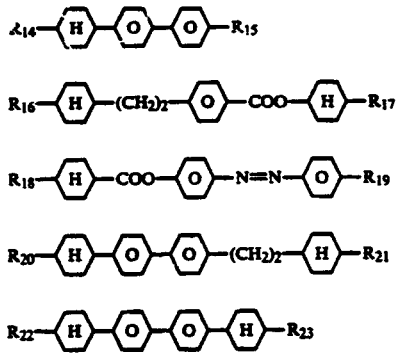

D wherein $R_{14}$ and $R_{15}$ are straight chain alkyl groups having from 1 to 12 carbon atoms, $R_{16}$ and $R_{17}$ are straight chain alkyl groups having from 1 to 9 carbon atoms, $R_{18}$ and $R_{19}$ are straight chain alkyl groups having from 1 to 8 carbon atoms, $R_{20}$ and $R_{21}$ are straight chain alkyl groups having from 1 to 7 carbon atoms and $R_{22}$ and $R_{23}$ are straight chain alkyl groups having from 1 to 10 carbon atoms.

The compounds D have a molecular configuration which is longer than that of the other compounds and have a high clearing point. Accordingly, by adding the compounds D, the clearing point of the liquid crystal composition is raised. Furthermore, similar to compounds C, compounds D also prevent deposition at low temperature. However, compounds D cause the applied voltage required to drive the liquid crystals to be higher, and it is necessary to add compounds B in a greater amount. Accordingly, the concentration of the compounds D should be kept to a minimum, as required.

The following is an explanation of the measuring method of the characteristics of the liquid crystal compositions of the twisted nematic mode shown below.

Figure 11:
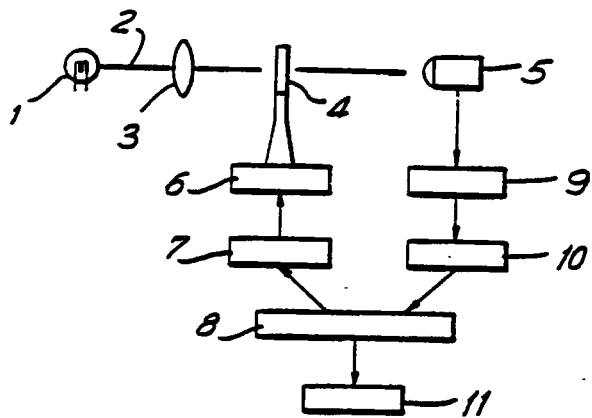
FIG. 11 illustrates the measuring device utilized in the experiments reported herein.

Reference is made to FIG. 11, wherein the measuring system used to record the electro-optical characteristics is shown. A measuring cell 4 formed of two glass plates each having a transparent electrode of, for example a lead oxide deposited by vapor deposition method on one side thereof with an organic thin film covering the electrodes with the surface being oriented was used. The two glass plates were fixed face to face and held with a frame made of nylon film which serves as a spacer for keeping a space between the two glasses as thick as desired into which a liquid crystal composition was to be sealed. A polarizer was fixed on both sides of the cell, with the direction of the polarizing axes aligned so that when a voltage was not applied, the cell transmitted light and when a voltage was applied, light was not transmitted.

In the following explanantion, the space between the two glass plates, i.e. the thickness of the liquid crystal layer, is referred to as the cell thickness indicated by d.

A light 2 emitted from a white light source 1 passes through a lens 3 to enter cell 4 at a right angle thereto.

A detector 5 disposed in the rear of cell 4 detects the brightness of light transmitted through cell 4. At this time, a voltage having an alternative square waveform of the frequency of 1 KH having an arbitrary effective voltage was applied to cell 4 by a driver circuit 6.

Figure 12:
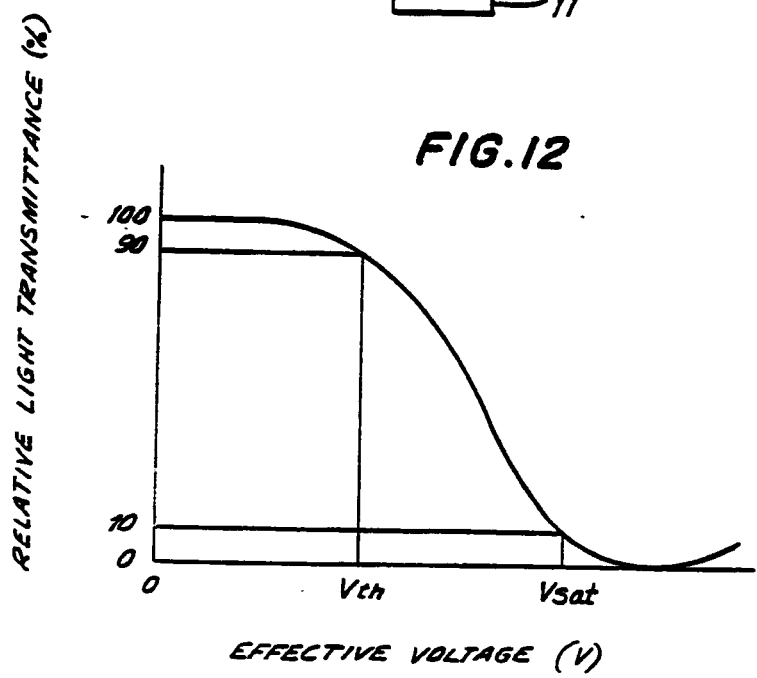
FIG. 12 illustrates the general relative light transmittance-effective voltage curve obtained by using the measuring device of FIG. 11.

In FIG. 12, the voltage-transmittance curves showing the results of the measurement by the measuring system shown in FIG. 11 is illustrated. In FIG. 12, the light transmittance at the time when the cell is brightest and darkest in the usual applied voltage range is indicated as 100% and 0%, respectively. By gradually increasing the applied voltage from the voltage when the light transmittance is 100%, the effective voltage when the light transmittance decreases by 10% is defined as the optical threshhold voltage (hereinafter referred to as the threshhold voltage) $V_{th}$. By further increasing the applied voltage, the effective voltage when the light transmittance decreases from 100% by 90% (that is, when the light transmittance becomes 10%) is defined as the optical saturated voltage (hereinafter referred to as the saturated voltage) $V_{sat}$. The rise (that is, steepness) of the voltage-transmittance curve near the threshhold voltage is defined as $\beta$ value as below:

$\beta = V_{sat}/V_{th}$

In accordance with the literature, the steepness $\beta$ approaches a minimum when the product $\Delta n \cdot d$ of the cell thickness $d(\mu)$ and the refraction anisotropy $\Delta n$ is between about 0.8 and 1.0 (Reference: Proceedings of the Third International Display Research Conference "Japan Display '83", page 320, 1983, Yoshio Yamazaki, Hiroshi Takeshita, Mitsyo Nagata and Yuko Miyachi, (SID). Accordingly, when a display of highest contrast is desired, it is most preferable to construct the liquid crystal display unit wherein the cell thickness d is selected so that $\Delta n \cdot d$ is between about 0.8 and 1.0. Thus, it was determined to measure and compare the steepness of the liquid crystal composition using the cell of a thickness as-described above.

With the above in mind in the tables in the following description of the compositions, the steepness, response speed and the threshhold voltage are shown by the value of the cell thickness when $\beta$ is a minimum (hereinafter referred to as the optimal cell thickness $d_{opt}$) and the minimum $\beta$ is referred to as the minimum steepness value $\beta$ min.

The response speed with respect to the change of the applied voltage is defined as follows. The effective voltage applied to the cell was switched from $V_{th}$ to $V_{sat}$ instantly, and under the usual condition, the time required for the light transmittance to change by 90% of the difference of the light transmittances with respect to $V_{th}$ and $V_{sat}$, respectively, (that is, the time required for the light transmittance to change from 90% to 18%) was expressed by $T_{on}$ in units of millisecond. Similarly, the effective voltage applied to the cell was switched from $V_{sat}$ to $V_{th}$ instantly, and under the usual condition, the time required for the light transmittance to change by 90% of the difference of the light transmittance with respect to $V_{sat}$ and $V_{th}$, respectively, (that is, the time required for the light transmittance to change from 10% to 82%) was expressed by $T_{off}$ in units of millisecond. The total T (millisecond) of $T_{on}$ and $T_{off}$ is a criteria of the response speed.

Since the average annual temperature in Tokyo and Naha are 15° C. and 22° C., respectively ("The Statistics of Japan" by Statistics Dept. of Prime Minister's Office, 1980, pp. 6-7), room temperature is assumed to be 20° C. and the measurement was done at 20° C.

In order to improve the uniformity of orientation, a small amount of cholesteric substance was added to the liquid crystal material in accordance with this invention which was sealed in the cell.

The stability of the nematic liquid crystal phase is expressed by the high temperature liquid crystal condition and the low temperature liquid crystal condition when the liquid crystal material was sealed in the cell. Specifically, the cell was placed on the thermostatic chamber and the stability of the nematic phase of the liquid crystal material at a temperature higher than the reference temperature 20° C. was called the high temperature liquid crystal phase at that temperature and the stable nematic phase was indicated by ◯ and the isotropic liquid phase was indicated by I. On the other hand, temperature of the thermostatic chamber in which the cell was placed was decreased by 5° C. per day starting with 20° C. Then the stability of the nematic liquid crystal phase at a temperature lower than 20° C. (that is, when the temperature of the thermostatic chamber was 0° C. or −20° C.) was defined to be the low temperature liquid crystal phase and the stable nematic phase was indicated by◯, the solid state of the condition when deposition occurred was indicated by and the smectic phase was indicated by Sm.

The clear point was measured by observing the work material sealed between a slide glass and a prepalate with a microscope as the temperature of the material was increased by 2° C. per minute by the set-for heating device.

Comparative Example 1

The compositions utilized in this Example are shown in Table 1 below.

Conventional composition 1 is a nematic liquid crystal composition composed of at least one compound represented by the general formula:

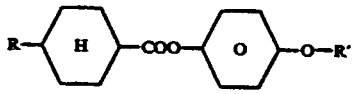

(hereinafter referred to as "ECH liquid crystal"); and at least one compound represented by the general formula:

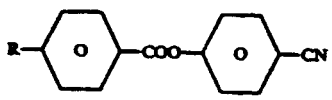

(hereinafter referred to as "p-E liquid crystal") wherein R and R' are straight chain alkyl groups having an arbitrary number of carbon atoms. The ECH and p-E liquid crystals correspond to Compound C and Compounds B, respectively. At present, nematic liquid crystal compounds based on similar compounds to B and C above or alternatively with another compounds represented by the general formula:

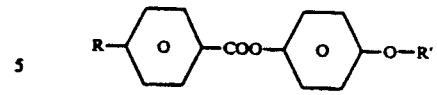

and so on are generally used.

The Comparative Example 1 composition is one including Compound A represented by the general formula:

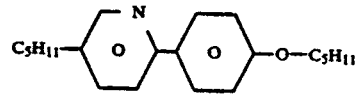

to a general nematic liquid crystal composition described above. Specifically, 20wt% of ECH in the Conventional Composition 1 was replaced by compound of the general formula:

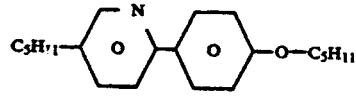

In this case, the concentration of p-E was same in the conventional composition 1 and Example 1 (12wt%), and accordingly, the two compositions had almost the same positive dielectric anisotropy and optical threshold voltage. Thus, the electro-optical characteristics of the both compositions were easily compared.

Figure 5:
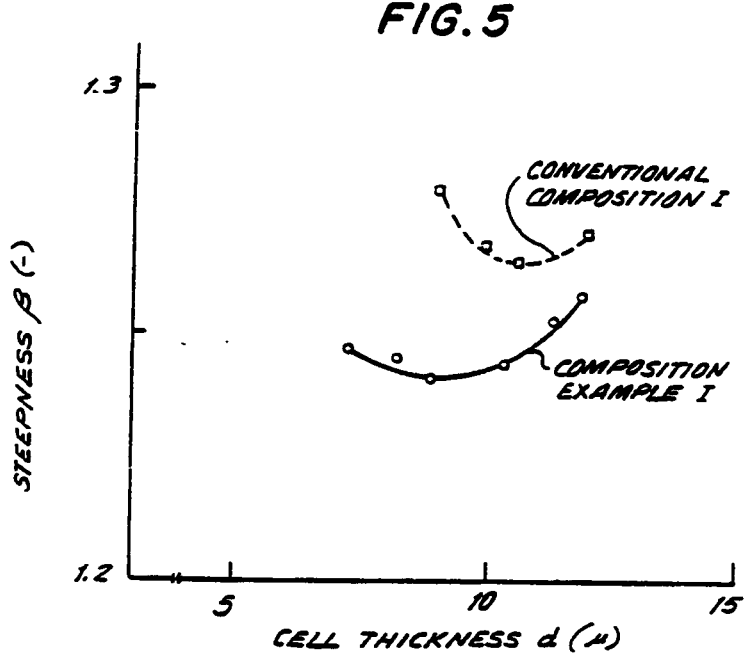
FIG. 5 illustrates the relationship between the steepness $\beta$ and the individual cell thickness D of Comparative Example 1.
Figure 6:
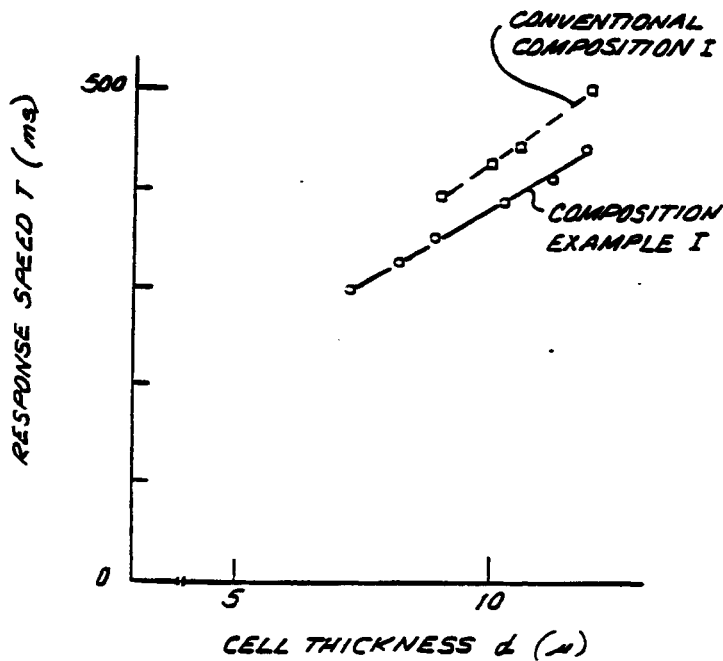
FIG. 6 illustrates the relationship between the response time T and the individual cell thickness D of Comparative Example 1.

The characteristics of the comparative compositions are shown by Table 1 and FIGS. 5 and 6. FIGS. 5 through 10 are illustrations which explain the achieved results in accordance with the invention.

As is shown in Table 1 and FIG. 6, the optimum steepness of Example 1 to which Compound A was added to the conventional composition is 1.265 and 1.242, which is a substantial improvement. In order to drive the liquid crystal cell in the dynamic mode so that the light transmittance at the selected electrodes and the non-selected electrodes are 10% or less and 90% or more, respectively, the maximum number of the scanning electrodes is 18 in the conventional composition while it is 22 in Compound Example 1.

As shown in FIG. 2, the response speed of Composition Example 1 is higher than the Conventional Example for all cell thicknesses.

With respect to the response speed, it is well known that $T_{on}$ is the time required for the light transmittance to change from 0% to 90% measured from the instant switching of the applied voltage from 0 to an arbitrary voltage $v$ (V), and $T_{off}$ is the time required for the light transmittance to change from 100% to 10% measured from the instant switching of applied voltage from $v$ to 0. $T_{on}$ and $T_{off}$ are expressed by the following equations (Reference: M. Schadt, Japan Learning and Stury Advancement Society, Organic Material for Science, The 142nd Committee A Group (Liquid Crystal Group), the material for the 11th Seminar, 1978):

$$T_{on} = \eta/(\epsilon_0 \Delta \epsilon E^2 - K(\pi/d)^2) = d^2 \eta/(\epsilon_0 \Delta \epsilon v^2 - K\pi^2) \qquad 2$$

$$T_{off} = \eta/K(\pi/d)^2 = d^2 \eta/K\pi^2 \qquad 3$$

wherein $\eta$ is the bulk viscosity, $\epsilon_0$ is the vacuum dielectric constant, $\Delta\epsilon$ is the relative dielectric anisotropy, E is the electric field, K is the elasticity constant term of $(K_{11} \times K_{22} - 2K_{22})/4$ and d is the cell thickness and $\eta, \Delta\epsilon$ and K are intrinsic to the liquid crystals.

The literature (Id., the material for the 31st Joint Seminar, 1984) shows that $T_{off}$ is proportional to the rotation viscosity $\gamma 1$ rather than to the mean bulk viscosity as shown by the following formula:

$$T_{off} \gamma 1/K$$

As shown above, there is a relationship between the response speed and viscosity, dielectric anisotropy and elasticity constant of the liquid crystal composition. In accordance with this invention, by adding Compound A, the physical properties of the nematic liquid crystal composition were changed, so that the response speed was shortened by the total effect ("Effect I" with respect to the response speed).

Figure 8:
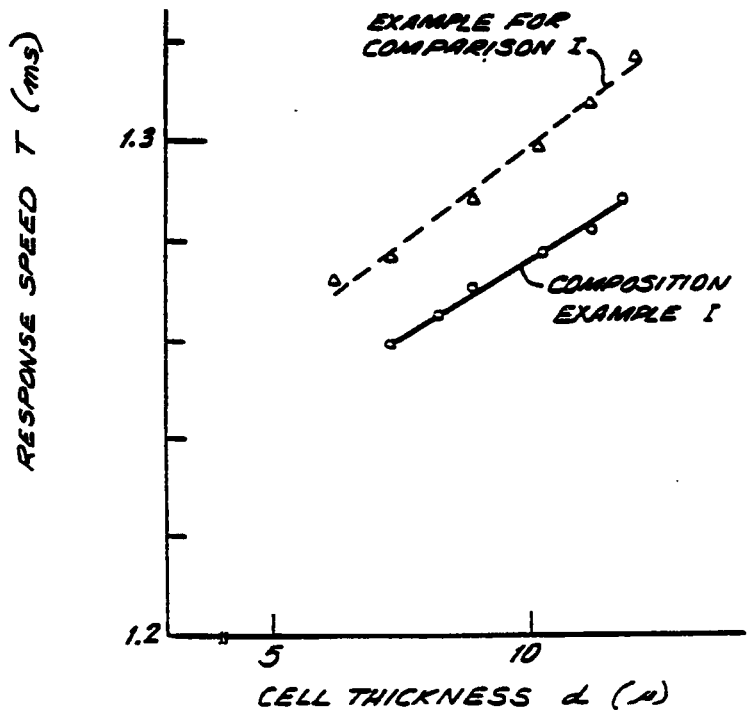
FIG. 8 illustrates the relationship between the response speed T and the individual cell thickness D of Comparative Example 1.
Figure 10:
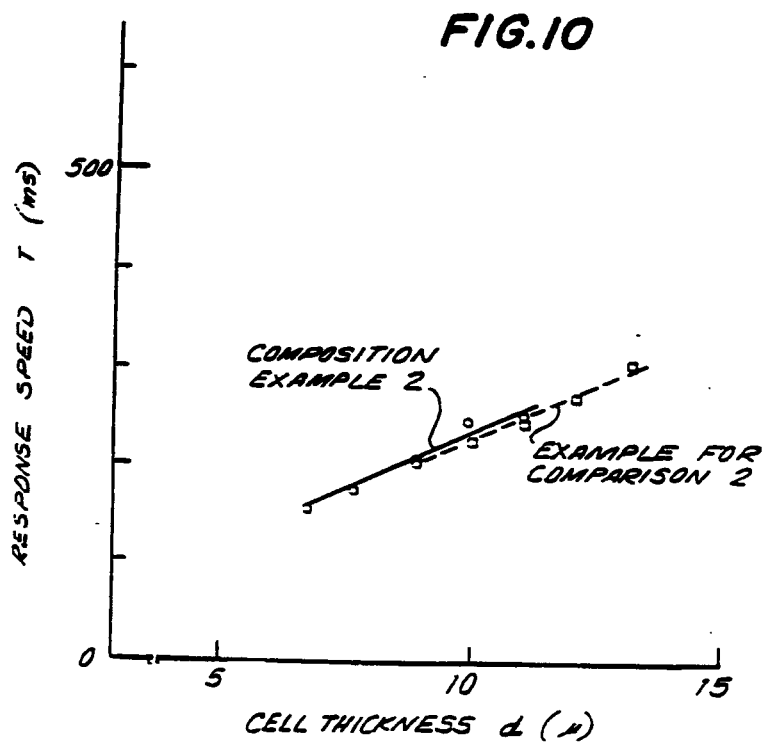
FIG. 10 illustrates the relationship between the response time T and the individual cell thickness D of Comparative Example 2.

As shown by Equations 2 and 3, $T_{on}$ and $T_{off}$ are lengthened in proportion to $d^2$. The response speed T as defined above is directly proportional to the cell thickness. FIGS. 6, 8 and 10 show that for a thinner cell, the faster response T and the thicker the cell, the slower the response T. Accordingly, when preparing a liquid crystal display unit using the same liquid crystal composition, the response speed may be shortened by making the cell thinner.

However, as mentioned before in connection with Equation 1, the steepness reaches it optimum when $\Delta n \cdot d$ is between about 0.8 and about 1.0. Thus, the optimal cell thickness is:

$$d_{opt} = 1\Delta n \qquad 5$$

As is apparent from this Equation 5, the nematic liquid crystal composition having a large $\Delta n$ is advantageous in that the cell thickness can be reduced, thereby improving the response speed.

$\Delta n$ of Conventional Composition 1 is 0.093 and the optimum cell thickness for the composition determined by the experiment was 10.6 (the value calculated by Equation 5 is 10.8$\mu$, which is close to the experiments result). On the other hand, $\Delta n$ of Compound Example 1 is 0.110 due to addition of Composition A. Consequently, the cell thickness is reduced to 8.9$\mu$. Thus, Compound Example 1 is advantageous with respect to the response speed ("Effect II" with respect to the response speed).

As explained above, Composition Example 1 is accordance with this invention has greatly improved response speed compared with the conventional composition 1 by the multiplied effect of Effects I and II.

The Example for Comparison 1 is described below:

Example for Comparison 1 is the composition formed by adding the pyrimidine derivative represented by the general formula:

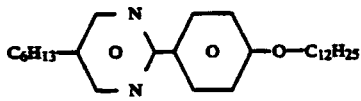

in place of the 2-phenylpyridine derivative as Composition Example 1. The pyrimidine derivative is known as the compound with the smallest elasticity constant ratio $K_{33}/K_{11}$ of 0.5 ($K_{33}$ and $K_{11}$ are the bend and spray elasticity is the continuum theory of F. C. Frank, respectively. Reference: Disc Faraddy Soc., 29, page 883, 1933) among the practically used liquid crystal compounds. (Reference: B. S. Scheuble, G. Bauer, Proceedings of the 3rd International Display Research Conference "Japan Display '83", page 224, 1983). The literature also shows that the smaller $K_{33}/K_{11}$ the nematic liquid crystal composition has, the smaller the steepness. (Reference: M. Schadt, P. R. Gerber, Z. Naturforsch. 27a, page 165, 1982).

Figure 7:
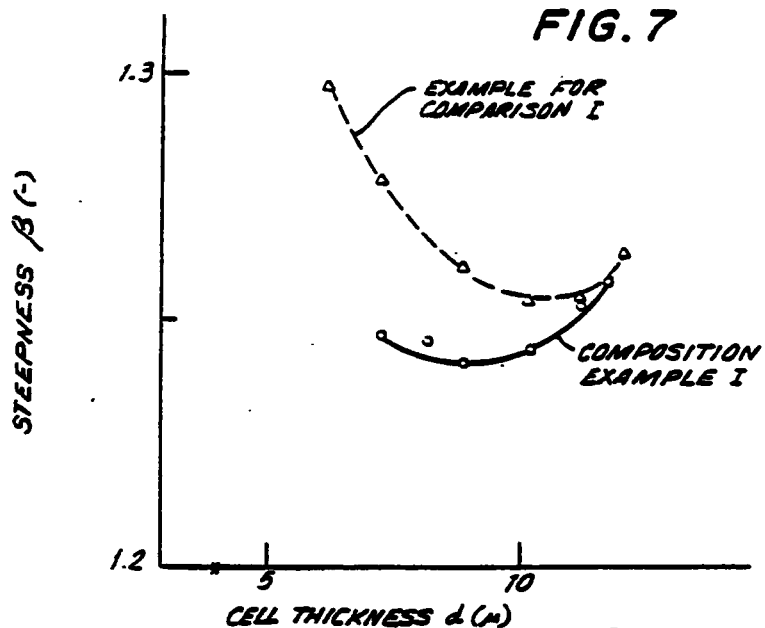
FIG. 7 illustrates the relationship between the steepness $\beta$ and the individual thickness D of Comparative Example 1.

As shown by the facts reported, the experiment demonstrated that Example for Comparison 1 to which the pyridine derivative was added presented the most improved steepness value compared to Conventional Composition 1. However, Composition Example 1 to which Compound A was added in accordance with this invention presented further improved steepness compared to Example for Comparison 1. FIG. 7 shows the relationship between the steepness value and cell thickness of Compositio Example 1 and Example for Comparison 1, respectively.

As mentioned above, the response speed of Composition Example 1 to which Composition A was added was shortened substantially. With respect to Example for Comparison 1 to which the pyrimidine compound was added, in spite of the fact that $\Delta n$ was relatively large, thereby slightly reducing the thickness of the cell, Effect I with respect to the response speed I was small. Accordingly, the response speed of Example for Comparison 1 was slower than Composition Example 1. FIG. 8 shows the relationship between the response speed T and the cell thickness d of Composition Example 1 and Example for Comparison 1, respectively.

The threshhold voltage for the optimum cell thickness of Composition Example 1, Conventional Composition 1 and Example for Comparison 1 are commonly between 2.55 and 2.59V. The clear point for each of these three compositions is over 60° C. and the high temperature liquid crystal phase is stable for all.

The low temperature liquid crystal phase at $-20°$ C. is unstable in Example for Comparison 1 and Conventional Composition 1. Specifically, in Example for Comparison 1 deposition occurs at temperatures as high as about 0° C. On the other hand, the low temperature liquid crystal phase of Composition Example 1 is stable and the stability of the nematic phase is maintained even at $-30°$ C.

As explained so far, Composition Example 1, compared with the Conventional Composition 1 and Example for Comparison 1, provides an excellent steepness value and response speed and presents an improved low temperature liquid crystal phase. Accordingly, the 2-phenylpyridine derivative which was added in Composition Example 1 is useful for improving these properties of the liquid crystal composition.

In Composition Example 1 as described above, the compound represented by the formula:

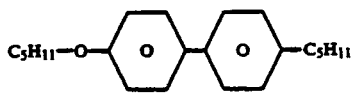

is the 2-phenylpyridine derivative (Compound A), the compound represented by the general formula:

as Compound B and the compound represented by the general formula:

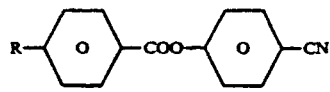

as Compound C were used wherein R and R' are straight chain alkyl groups having an arbitrary number of carbon atoms.

However, the 2-phenylpyridine compound used with Compound B and Compound C, are not limited to those shown, but other compounds described are also applicable to provide excellent nematic liquid crystal compositions.

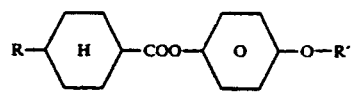

TABLE 1

| Composition (wt %) | Conventional Composition 1 | Compound Example 1 | Example for Comparison 1 |
|---|---|---|---|
| A C$_5$H$_{11}$—⬡(N)—⬡—O—C$_5$H$_{11}$ | 0 | 20.0 | 0 |
| C$_6$H$_{13}$—⬡(N,N)—⬡—O—C$_{12}$H$_{25}$ | 0 | 0 | 20.0 |
| B C$_2$H$_5$—⬡—COO—⬡—CN | 6.0 | 6.0 | 6.0 |
| C$_4$H$_9$—⬡—COO—⬡—CN | 6.0 | 6.0 | 6.0 |
| C C$_3$H$_7$—⬢(H)—COO—⬡—O—C$_2$H$_5$ | 1.6 | 1.2 | 1.2 |
| C$_3$H$_7$—⬢(H)—COO—⬡—O—C$_4$H$_9$ | 5.6 | 4.3 | 4.3 |
| C$_4$H$_9$—⬢(H)—COO—⬡—O—CH$_3$ | 4.1 | 3.2 | 3.2 |
| C$_4$H$_9$—⬢(H)—COO—⬡—O—C$_2$H$_5$ | 3.5 | 2.7 | 2.7 |
| C$_4$H$_9$—⬢(H)—COO—⬡—O—C$_5$H$_{11}$ | 4.2 | 3.3 | 3.3 |
| C$_4$H$_9$—⬢(H)—COO—⬡—O—C$_6$H$_{13}$ | 18.1 | 14.0 | 14.0 |

TABLE 1-continued

| | Conventional Composition 1 | Compound Example 1 | Example for Comparison 1 |
|---|---|---|---|
| 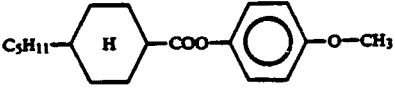 $C_5H_{11}$—H—COO—◯—O—$CH_3$ | 4.4 | 3.4 | 3.4 |
| 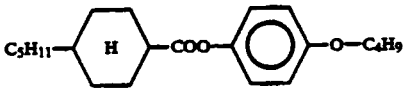 $C_5H_{11}$—H—COO—◯—O—$C_4H_9$ | 11.8 | 9.1 | 9.1 |
| 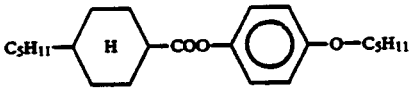 $C_5H_{11}$—H—COO—◯—O—$C_5H_{11}$ | 8.6 | 6.7 | 6.7 |
| 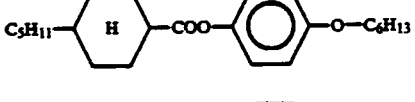 $C_5H_{11}$—H—COO—◯—O—$C_6H_{13}$ | 16.3 | 12.6 | 12.6 |
| 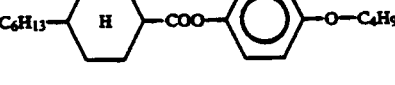 $C_6H_{13}$—H—COO—◯—O—$C_4H_9$ | 9.7 | 7.5 | 7.5 |
| Birefringence Δn (—) | 0.93 | 0.110 | 0.104 |
| Optimal Cell Thickness dopt (μ) | 10.6 | 8.9 | 10.2 |
| Threshold Voltage Vth (V) | 2.59 | 2.57 | 2.55 |
| Minimum Steepness βmin (—) | 1.265 | 1.241 | 1.254 |
| Response Time T (ms) | 444 | 325 | 495 |
| High Temp. Liq. Cry. Phase (60° C.) | | | |
| Low Temp. Liq. Cry. Phase (−20° C.) | x | | x |

Composition Example 2

Table 2 shows the compositions tested and the properties of Composition Example 2 and Conventional Composition 2.

Conventional Composition 2 is used as a nematic liquid crystal composition of fast response speed. Conventional Composition 2 differs from Conventional Composition 1 as it includes compounds represented by the general formula:

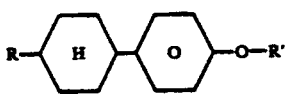

R—H—◯—O—R' as Compound C'; and a compound represented by the general formula:

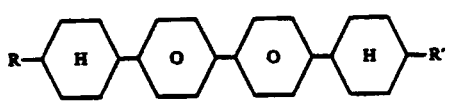

R—H—◯—O—◯—O—H—R' as Compound D was further added.

Composition Example 2 is formed by adding a compound represented by the general formula:

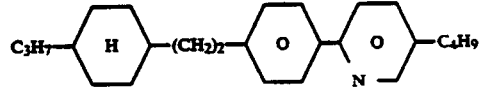

$C_3H_7$—H—$(CH_2)_2$—◯—◯—$C_4H_9$
                               N in place of 20wt% of Compound C' in the same manner as in composition Example 1.

Figure 9:
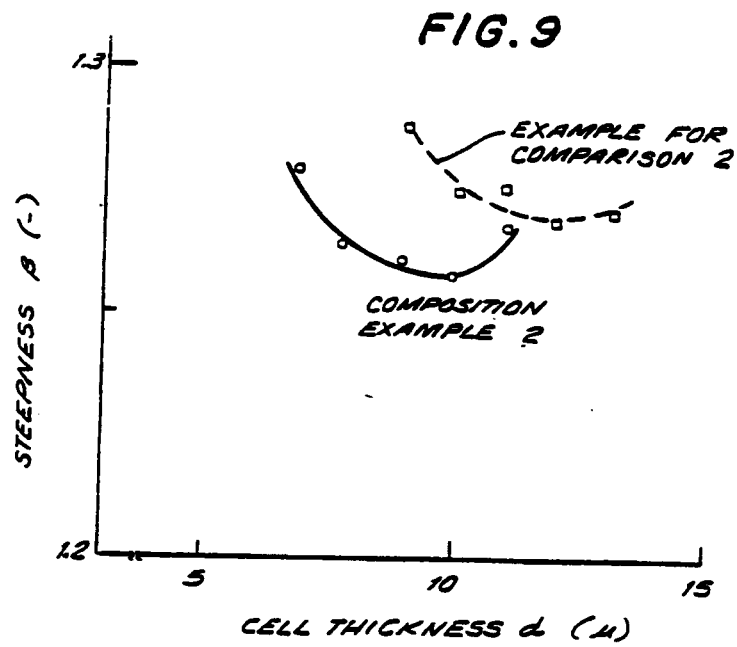
FIG. 9 illustrates the relationship between the steepness $\beta$ and the individual cell thickness D of Comparative Example 2.

FIG. 9 shows the relationship between the steepness value and the cell thickness of Conventional Composition 2 and Composition Example 2, respectively. The steepness of Composition Example 2 is superior to Example for Comparison 2 with the minimum steepness β min improved by 0.011.

As shown in FIG. 10, the response speed of Composition Example 2 and Example for Comparison 2 are about the same. However, as shown by Table 2, birefringence Δn is greater for Composition Example 2 than Example for Comparison 2. Consequently, the optimum cell thickness was reduced by about 2μ by using Composition Example 2. Accordingly, the response speed of Composition Example 2 was reduced by over 40 ms compared to Example for Comparison 2.

The Conventional Composition 2 has a clear point of 66° C. without deposition if the temperature is higher than −20° C. Thus, a high temperature liquid crystal phase at 60° C. and a low temperature liquid crystal phase of the Conventional Composition 2 are both completely stable. However, under more harsh conditions, for example at 80° C. and −40° C., the high temperature liquid crystal phase and the low temperature liquid crystal phase are not satisfactory.

On the other hand, Composition Example 2 has a clear point of 82° C. without deposition at temperatures lower than −40° C. Accordingly, Composition Example 2 presents a satisfactory high temperature liquid crystal phase and low temperature liquid crystal phase at 80° C. and −40° C., respectively. Thus, Composition Example 2 is suitable for use under harsh temperature conditions, such as for a display device used in a car.

The two Effects with respect to the response speed I and II, as defined above, are improved physical properties due to addition of the 2-phenylpyridine derivatives. These improvements are consistently achieved when added to the generally used liquid crystal compounds and liquid crystal compositions. Accordingly, in the following Composition Examples the improved response time will not be referred to and only the steepness and the other improvements will be described.

TABLE 2

| Composition (wt %) | Conventional Composition 2 | Composition Example 2 |
|---|---|---|
| A  $C_3H_7$—⬡—$(CH_2)_2$—⌬—⌬—$C_4H_9$ | 0 | 20.0 |
| B  $C_2H_5$—⌬—COO—⌬—CN | 6.1 | 6.1 |
|    $C_4H_9$—⌬—COO—⌬—CN | 6.1 | 6.1 |
| C  $C_3H_7$—⬡—⌬—O—$C_2H_5$ | 19.3 | 10.0 |
|    $C_3H_7$—⬡—⌬—O—$C_4H_9$ | 19.0 | 9.8 |
|    $C_3H_7$—⬡—⌬—O—$C_5H_{11}$ | 21.2 | 10.9 |
|    $C_4H_9$—⬡—⌬—O—$CH_3$ | 11.3 | 5.8 |
|    $C_4H_9$—⬡—⌬—O—$C_2H_5$ | 12.3 | 6.4 |
|    $C_5H_{11}$—⬡—⌬—O—$C_2H_5$ | 16.8 | 8.7 |
| D  $C_5H_{11}$—⬡—⌬—⬡—$C_3H_7$ | 16.2 | 16.2 |
| Birefringence Δn (—) | 0.105 | 0.126 |
| Optimal Cell Thickness dopt (μ) | 12.0 | 9.9 |
| Threshold Voltage Vth (V) | 2.64 | 2.98 |
| Minimum Steepness βmin (—) | 1.269 | 1.258 |
| Response Time T (ms) | 268 | 224 |
| High Temp. Liq Cry Phase (60° C.) | | |
| High Temp. Liq Cry Phase (80° C.) | l | |
| Low Temp. Liq Cry Phase (−20° C.) | | |
| Low Temp. Liq Cry Phase (−40° C.) | x | |

Composition Examples 3 to 6

Table 3 shows the compositions and the physical properties of Composition Examples 3 to 6.

Example for Comparison 3 includes only 2-phenylpyridine derivatives and presents a nematic liquid crystal temperature range with a liquid crystal phase having a stable high temperature limit. The clear point of this Composition is 64° C. However, since the melting point is as high as 52° C., the nematic liquid crystal phase is stable only at high temperature. That is, at 20° C., this composition is the solid state and consequently it is not driven by the electric field and thereby the electro-optical property thereof could not be measured.

Example for Comparison 4 includes only p-E liquid crystals and presents the nematic liquid crystal phase over the temperature range between 10° C. and 42° C. Thus, the electro-optical properties were measured. The threshhold voltage $V_{th}$ was 0.74V, which is very low. The minimum steepness $\beta$ min is 1.28, which is inferior compared to the Conventional Composition 1 as shown by Table 1 before.

The liquid crystal composition including only 2-phenylpyridine derivatives or only p-E as above have a narrow liquid crystal temperature range and the electro-optical properties cannot be measured at room temperature or if can, the steepness value is poor.

Composition Examples 3 to 6 are nematic liquid crystal compositions including 2-phenylpyridine derivatives and p-E liquid crystals and conventional nematic liquid crystal compounds. The proportion of the mixing rate of the 2-phenylpyridine derivatives and p-E liquid crystals was varied over the range from 80wt% to 20wt% to 20wt% to 80wt% in these examples. Composition Examples 3 to 6 present a nematic liquid crystal phase at 0° C. and 40° C. as well as at room temperature. The threshhold voltage was relatively low, such as from 2.05 to 1.0 V, and the example including p-E liquid crystal having the highest positive dielectric anisotropy among those listed in Table 1 had an extremely low threshhold voltage of 1.01V. The steepness $\beta$ of these examples is between 1.24 and 1.26 which is good. Composition Example 1 including a 2-phenylpyridine derivative in the largest amount among those listed in Table 1 had the best minimum steepness $\beta$ min of 1.24.

Comparing Composition Examples 3 to 6 to Examples for Comparison 3 and 4 including only Composition A or only p-E liquid crystal respectively, the following advantages are attained by Composition Examples 3 to 6. The nematic liquid crystal temperature range is expanded considerably and a display cell using the compositions in accordance with this invention can be driven over the temperature range from 20° C. below to 20° C. above room temperature.

Moreover, notwithstanding that the make-up of the compositions in accordance with this invention is extremely simple such as that so-called Nn liquid crystal compounds and Np liquid crystal compounds are mixed, merely by using Compound A as a Nn liquid crystal compound, the minimum steepness value is also greatly improved compared with Example for Comparison 4 and Conventional Composition 1.

As Compound B in the compositions in accordance with the invention, the compounds indicated by B below, including p-E liquid crystal used in Composition Examples 3 to 6, are especially effective.

B

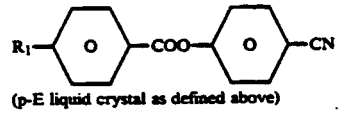

(p-E liquid crystal as defined above)

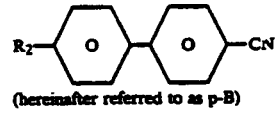

(hereinafter referred to as p-B)

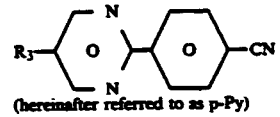

(hereinafter referred to as p-Py)

(hereinafter referred to as p-P)

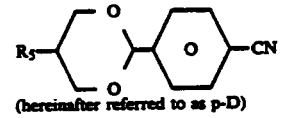

(hereinafter referred to as p-D)

wherein $R_1$ is a straight chain alkyl group having from 1 to 10 carbon atoms and $R_2$, $R_3$, $R_4$ and $R_5$ are straight chain alkyl groups having from 1 to 12 carbon atoms.

TABLE 3

| | Example for Comparison | Composition Example | | | | Example for Comparison |
|---|---|---|---|---|---|---|
| | 3 | 3 | 4 | 5 | 6 | 4 |
| A  C₂H₅—⟨N⟩—⟨⟩—O—C₆H₁₃ | 6.2 | 5.0 | 3.7 | 2.5 | 1.2 | 0 |
| C₅H₁₁—⟨N⟩—⟨⟩—O—C₂H₅ | 0.8 | 0.6 | 0.4 | 0.3 | 0.2 | 0 |
| C₅H₁₁—⟨N⟩—⟨⟩—O—C₄H₉ | 1.4 | 1.2 | 0.9 | 0.6 | 0.3 | 0 |

TABLE 3-continued

| | Example for Comparison 3 | Composition Example 3 | 4 | 5 | 6 | Example for Comparison 4 |
|---|---|---|---|---|---|---|
| C₅H₁₁–[pyridine]–[phenyl]–O–C₅H₁₁ | 8.0 | 6.4 | 4.8 | 3.2 | 1.6 | 0 |
| C₅H₁₁–[pyridine]–[phenyl]–O–C₆H₁₃ | 29.4 | 23.5 | 17.7 | 11.7 | 5.9 | 0 |
| C₄H₉–[pyridine]–[phenyl]–O–C₆H₁₃ | 15.7 | 12.6 | 9.4 | 6.3 | 3.1 | 0 |
| C₄H₉–[pyridine]–[phenyl]–O–C₅H₁₁ | 38.5 | 30.7 | 23.1 | 15.4 | 7.7 | 0 |
| B  C₂H₅–[phenyl]–COO–[phenyl]–CN | 0 | 10.0 | 20.0 | 30.0 | 40.0 | 0 |
| C₄H₉–[phenyl]–COO–[phenyl]–CN | 0 | 10.0 | 20.0 | 30.0 | 40.0 | 0 |
| Threshold Voltage Vth (V) | — | 2.05 | 1.44 | 1.17 | 1.01 | 0.74 |
| Minimum Steepness β min (—) | — | 1.24 | 1.25 | 1.25 | 1.26 | 1.28 |
| High Temp. Liq. Crys. Phase (40° C.) | | | | | | 1 |
| Low Temp. Liq. Crys. Phase (0° C.) | x | | | | | x |

Composition Examples 7 through 17

Composition Examples 7 through 17 are the compositions in which the compounds represented by the general formula:

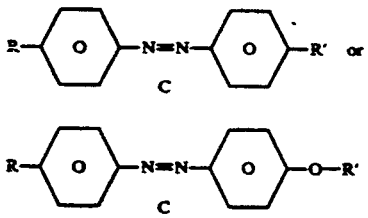

were used as Compound C. The compositions and the physical properties of these compositions are shown by Tables 3A to 8.

As Compound B, the various liquid crystal compounds shown in the last paragraph of the description of Composition Examples 3 to 6 were used and the concentrations thereof were varied as indicated. Various threshhold voltages ranging from 1.25 to 3.16 V were observed.

The minimum steepness value of Composition Examples 7 through 17 was between 1.24 and 1.26, which is superior to the conventional examples.

Moreover, the high temperature liquid crystal phase at 40° C. and the low temperature liquid crystal phase at 0° C. of these examples were both sufficiently good.

TABLE 3A

| | Composition Example 7 |
|---|---|
| Composition (wt %) | |
| A 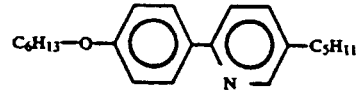 | 10.0 |

TABLE 3A-continued
| | | Composition Example 7 |
|---|---|---|
| B | 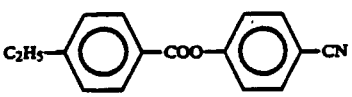 | 5.0 |
| | 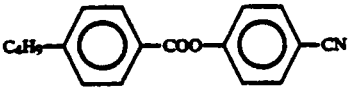 | 5.0 |
| C | 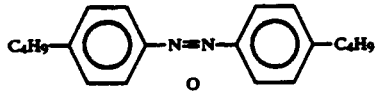 | 17.5 |
| | 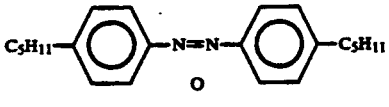 | 17.5 |
| | 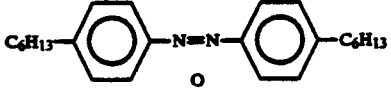 | 17.5 |
| | 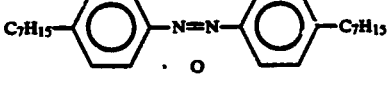 | 17.5 |
| D |  | 10.0 |
| Threshold Voltage Vth (V) | | 2.97 |
| Minimum Steepness βmin | | 1.24 |
| High Temp. Liquid Crystal Phase (40° C.) | | |
| Low Temp. Liquid Crystal Phase (0° C.) | | |
TABLE 4
| | | Composition Examples | |
|---|---|---|---|
| | | 8 | 9 |
| | Composition (wt %) | | |
| A | 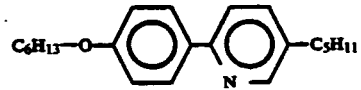 | 10.0 | 10.0 |
| B | 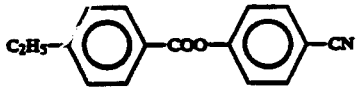 | 2.8 | 8.7 |
| | 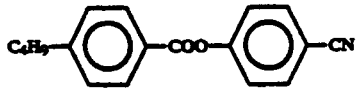 | 3.2 | 9.6 |
| | 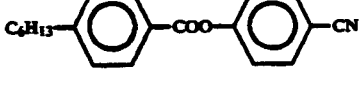 | 3.3 | 10.1 |

TABLE 4-continued
| | Composition Examples | |
|---|---|---|
| | 8 | 9 |
| C 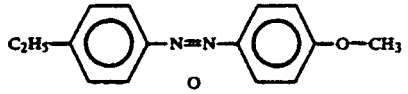 | 1.2 | 0.9 |
| 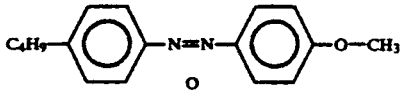 | 16.7 | 12.8 |
| 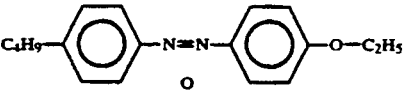 | 18.4 | 14.0 |
| 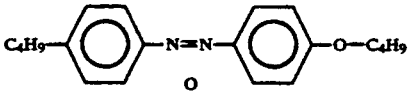 | 8.4 | 6.4 |
| 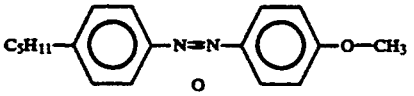 | 36.0 | 27.5 |
| Threshold Voltage Vth | 2.59 | 1.25 |
| Minimum Steepness βmin | 1.26 | 1.26 |
| High Temp. Liquid Crystal Phase (40° C.) | | |
| Low Temp. Liquid Crystal Phase (0° C.) | | |
TABLE 5
| | Composition Example | |
|---|---|---|
| | 10 | 11 |
| Composition (wt %) | | |
| A 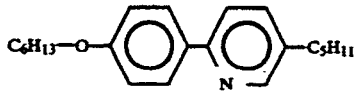 | 10.0 | 10.0 |
| B  | 1.5 | 4.8 |
| 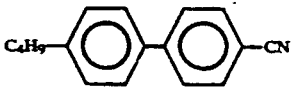 | 4.9 | 15.2 |
|  | 1.7 | 5.4 |
| C 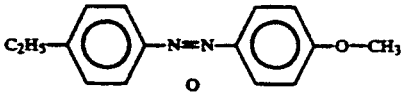 | 1.2 | 0.9 |
| 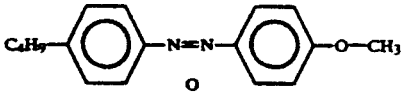 | 17.0 | 13.4 |

TABLE 5-continued

| | Composition Example | |
|---|---|---|
| | 10 | 11 |
| 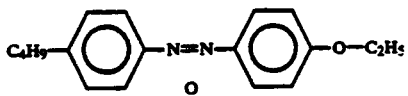 C₄H₉—⟨⟩—N=N—⟨⟩—O—C₂H₅ (O on N) | 18.7 | 14.7 |
| 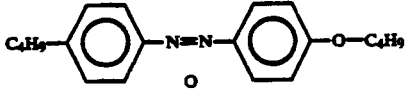 C₄H₉—⟨⟩—N=N—⟨⟩—O—C₄H₉ (O on N) | 8.5 | 6.8 |
| 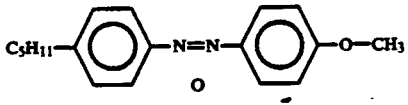 C₅H₁₁—⟨⟩—N=N—⟨⟩—O—CH₃ (O on N) | 36.5 | 28.8 |
| Threshold Voltage Vth | 3.08 | 1.74 |
| Minimum Steepness β min | 1.25 | 1.24 |
| High Temp. Liquid Crystal Phase (40° C.) | | |
| Low Temp. Liquid Crystal Phase (0° C.) | | |

TABLE 6

| | | Composition Example | |
|---|---|---|---|
| | Composition (wt %) | 12 | 13 |
| A |  C₆H₁₃—O—⟨⟩—⟨⟩(N)—C₅H₁₁ | 10.0 | 10.0 |
| B | 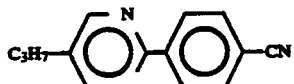 C₃H₇—⟨⟩(N,N)—⟨⟩—CN | 1.5 | 4.8 |
| | 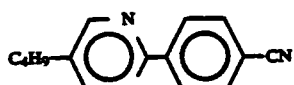 C₄H₉—⟨⟩(N,N)—⟨⟩—CN | 4.9 | 15.2 |
| | 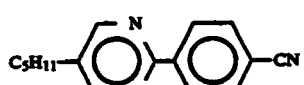 C₅H₁₁—⟨⟩(N,N)—⟨⟩—CN | 1.7 | 5.4 |
| C | 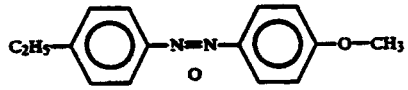 C₂H₅—⟨⟩—N=N—⟨⟩—O—CH₃ (O on N) | 1.2 | 0.9 |
| | 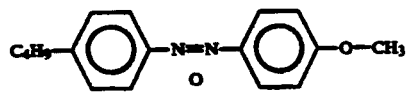 C₄H₉—⟨⟩—N=N—⟨⟩—O—CH₃ (O on N) | 17.0 | 13.4 |
| | 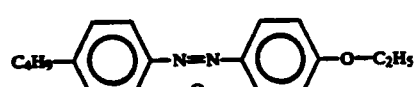 C₄H₉—⟨⟩—N=N—⟨⟩—O—C₂H₅ (O on N) | 18.7 | 14.7 |
| |  C₄H₉—⟨⟩—N=N—⟨⟩—O—C₄H₉ (O on N) | 8.5 | 6.8 |

TABLE 6-continued

| Composition (wt %) | Composition Example | |
|---|---|---|
| | 12 | 13 |
| C₅H₁₁—⟨⟩—N=N(O)—⟨⟩—O—CH₃ | 36.5 | 28.8 |
| Threshold Voltage Vth | 2.35 | 1.69 |
| Minimum Steepness βmin | 1.25 | 1.24 |
| High Temp. Liquid Crystal Phase (40° C.) | | |
| Low Temp. Liquid Crystal Phase (0° C.) | | |

TABLE 7

| | Composition (wt %) | Composition Example | |
|---|---|---|---|
| | | 14 | 15 |
| A | C₆H₁₃—O—⟨⟩—⟨N⟩—C₅H₁₁ | 10.0 | 10.0 |
| B | C₃H₇—⟨H⟩—⟨⟩—CN | 1.5 | 4.8 |
| | C₄H₉—⟨H⟩—⟨⟩—CN | 5.0 | 15.5 |
| | C₅H₁₁—⟨H⟩—⟨⟩—CN | 1.8 | 5.4 |
| C | C₂H₅—⟨⟩—N=N(O)—⟨⟩—O—CH₃ | 1.2 | 0.9 |
| | C₄H₉—⟨⟩—N=N(O)—⟨⟩—O—CH₃ | 17.0 | 13.3 |
| | C₄H₉—⟨⟩—N=N(O)—⟨⟩—O—C₂H₅ | 18.6 | 14.6 |
| | C₄H₉—⟨⟩—N=N(O)—⟨⟩—O—C₄H₉ | 8.5 | 7.0 |
| | C₅H₁₁—⟨⟩—N=N(O)—⟨⟩—O—CH₃ | 36.4 | 28.5 |
| Threshold Voltage Vth | | 3.16 | 1.61 |
| Minimum Steepness βmin | | 1.25 | 1.26 |
| High Temp. Liquid Crystal Phase (40° C.) | | | |
| Low Temp. Liquid Crystal Phase (0° C.) | | | |

TABLE 8

| Composition (wt %) | Composition Example 16 | Composition Example 17 |
|---|---|---|
| A: $C_6H_{13}$—O—⟨phenyl⟩—⟨pyridyl-N⟩—$C_5H_{11}$ | 10.0 | 10.0 |
| B: $C_3H_7$—CH(—O—CH$_2$—O—)—⟨phenyl⟩—CN (1,3-dioxane) | 1.9 | 4.9 |
| $C_4H_9$—CH(—O—CH$_2$—O—)—⟨phenyl⟩—CN | 5.0 | 15.7 |
| $C_5H_{11}$—CH(—O—CH$_2$—O—)—⟨phenyl⟩—CN | 1.7 | 5.5 |
| C: $C_2H_5$—⟨phenyl⟩—N=N(O)—⟨phenyl⟩—O—CH$_3$ | 1.2 | 0.9 |
| $C_4H_9$—⟨phenyl⟩—N=N(O)—⟨phenyl⟩—O—CH$_3$ | 16.9 | 13.3 |
| $C_4H_9$—⟨phenyl⟩—N=N(O)—⟨phenyl⟩—O—$C_2H_5$ | 18.5 | 14.5 |
| $C_4H_9$—⟨phenyl⟩—N=N(O)—⟨phenyl⟩—O—$C_4H_9$ | 8.5 | 6.7 |
| $C_5H_{11}$—⟨phenyl⟩—N=N(O)—⟨phenyl⟩—O—CH$_3$ | 36.3 | 28.5 |
| Threshold Voltage $V_{th}$ | 2.75 | 1.49 |
| Minimum Steepness $\beta_{min}$ | 1.25 | 1.25 |
| High Temp. Liquid Crystal Phase (40° C.) | | |
| Low Temp. Liquid Crystal Phase (0° C.) | | |

Composition Examples 18 through 21

Table 9 shows Composition Examples 18 to 21. Composition Examples 18 through 21 are nematic liquid crystal compositions including ECH liquid crystals as Compound C and p-E liquid crystals as Compound B and varying the concentration in order to change the threshhold voltage. By changing the concentration of p-E from 2wt% in Composition Example 18 to 32wt% in Composition Example 21, the threshhold voltage was lowered from 6.47 V to 1.36 V.

The saturated voltage of Composition Example 21 was 1.70 V. When Composition Example 21 was driven by a button-type carbon fluoride battery (3 V) power source without using a booster circuit, the cell can be driven with ⅓ bias to ¼ duty.

Contrary to the threshhold voltage, the most improved steepness value in Composition Example 18 included a minimum amount of p-E liquid crystal. Accordingly, in order to increase the number of the scanning lines which can be driven while maintaining good display contrast, the steepness should be improved. Thus, a composition wherein the concentration of p-E is as small as possible is desirable. However, since the upper limit of the threshhold voltage and the saturated voltage is limited by the rated output voltage of the driver circuit, the lower limit of the concentration of p-E is also limited.

As demonstrated by Composition Examples 18 to 21, similarly to Composition Examples 3 to 6 and 8 to 17, even when ECH liquid crystal is used as Compound C, the threshhold voltage varies freely according to the concentration of Compound B. Accordingly, the steepness is improved and the nematic liquid crystal temperature range is expanded compared to the conventional compositions.

TABLE 9

| Composition (wt %) | Composition Example | | | |
|---|---|---|---|---|
| | 18 | 19 | 20 | 21 |
| A | | | | |
| $C_5H_{11}$–⟨N⟩–⟨⟩–O–$C_5H_{11}$ | 10.0 | 10.0 | 10.0 | 10.0 |
| $C_5H_{11}$–⟨N⟩–⟨⟩–O–$C_6H_{13}$ | 10.0 | 10.0 | 10.0 | 10.0 |
| B | | | | |
| $C_2H_5$–⟨⟩–COO–⟨⟩–CN | 1.0 | 3.0 | 8.1 | 16.0 |
| $C_4H_9$–⟨⟩–COO–⟨⟩–CN | 1.0 | 3.0 | 8.1 | 16.0 |
| C | | | | |
| $C_3H_7$–⟨H⟩–COO–⟨⟩–O–$C_2H_5$ | 1.4 | 1.3 | 1.2 | 0.9 |
| $C_3H_7$–⟨H⟩–COO–⟨⟩–O–$C_4H_9$ | 4.9 | 4.7 | 4.0 | 3.0 |
| $C_4H_9$–⟨H⟩–COO–⟨⟩–O–$CH_3$ | 3.6 | 3.4 | 2.9 | 2.2 |
| $C_4H_9$–⟨H⟩–COO–⟨⟩–O–$C_2H_5$ | 3.1 | 2.9 | 2.5 | 1.9 |
| $C_4H_9$–⟨H⟩–COO–⟨⟩–O–$C_5H_{11}$ | 3.8 | 3.6 | 3.1 | 2.7 |
| $C_4H_9$–⟨H⟩–COO–⟨⟩–O–$C_6H_{13}$ | 16.1 | 15.3 | 13.1 | 9.9 |
| $C_5H_{11}$–⟨H⟩–COO–⟨⟩–O–$CH_3$ | 3.9 | 3.7 | 3.2 | 2.4 |
| $C_5H_{11}$–⟨H⟩–COO–⟨⟩–O–$C_4H_9$ | 10.5 | 9.9 | 8.6 | 6.3 |

TABLE 9-continued

| Composition (wt %) | Composition Example | | | |
|---|---|---|---|---|
| | 18 | 19 | 20 | 21 |
| $C_5H_{11}$–⬡H–COO–⬡–O–$C_5H_{11}$ | 7.6 | 7.3 | 6.3 | 4.6 |
| $C_5H_{11}$–⬡H–COO–⬡–O–$C_6H_{13}$ | 14.5 | 13.7 | 11.8 | 8.8 |
| $C_6H_{13}$–⬡H–COO–⬡–O–$C_4H_9$ | 8.6 | 8.2 | 7.1 | 5.3 |
| Threshold Voltage Vth (V) | 6.47 | 3.74 | 2.18 | 1.36 |
| Minimum Steepness βmin (—) | 1.23 | 1.24 | 1.25 | 1.25 |
| High Temp. Liquid Crystal Phase (60° C.) | | | | |
| Low Temp. Liquid Crystal Phase (−20° C.) | | | | |

Composition Example 22

Table 10 shows Composition Example 22 which is a nematic liquid crystal composition including four different 2-phenylpyridine derivatives. The threshhold voltage of Composition Example 22 was 2.6 V level, which is the same as that of Composition Example 1 including one 2-phenylpyridine derivative and which was extremely good. Moreover, this composition presents a stable nematic liquid crystal phase at low temperature (−20° C.) and at high temperature (60° C.). Additionally, even at temperatures lower than −30° C., the nematic liquid crystal phase is stable.

As explained above, in accordance with this invention, regardless of the number of 2-phenylpyridine compounds included and regardless of the difference between the substituent groups as described above, the nematic liquid crystal compositions having improved electro-optical characteristics and improved stability of the high and low temperature liquid crystal phase are provided.

TABLE 10

| Composition (wt %) | Composition Example 22 |
|---|---|
| A $C_5H_{11}$–⬡N–⬡–O–$C_4H_9$ | 5.0 |
| $C_5H_{11}$–⬡N–⬡–O–$C_5H_{11}$ | 5.0 |
| $C_4H_9$–⬡N–⬡–O–$C_6H_{13}$ | 5.0 |

TABLE 10-continued

| Composition (wt %) | Composition Example 22 |
|---|---|
| $C_5H_{11}$–⬡N–⬡–O–$C_5H_{13}$ | 5.0 |
| B $C_2H_5$–⬡–COO–⬡–CN | 6.0 |
| $C_4H_9$–⬡–COO–⬡–CN | 6.0 |
| C $C_3H_7$–⬡H–COO–⬡–O–$C_2H_5$ | 1.2 |
| $C_3H_7$–⬡H–COO–⬡–O–$C_4H_9$ | 4.3 |
| $C_4H_9$–⬡H–COO–⬡–O–$CH_3$ | 3.2 |
| $C_4H_9$–⬡H–COO–⬡–O–$C_2H_5$ | 2.7 |
| $C_4H_9$–⬡H–COO–⬡–O–$C_5H_{11}$ | 3.3 |

TABLE 10-continued

| Composition (wt %) | Composition Example 23 |
|---|---|
| C₄H₉—⟨H⟩—COO—⟨◯⟩—O—C₆H₁₃ | 14.0 |
| C₅H₁₁—⟨H⟩—COO—⟨◯⟩—O—CH₃ | 3.4 |
| C₅H₁₁—⟨H⟩—COO—⟨◯⟩—O—C₄H₉ | 9.1 |
| C₅H₁₁—⟨H⟩—COO—⟨◯⟩—O—C₅H₁₁ | 6.7 |
| C₅H₁₁—⟨H⟩—COO—⟨◯⟩—O—C₆H₁₃ | 12.6 |
| C₆H₁₃—⟨H⟩—COO—⟨◯⟩—O—C₄H₉ | 7.5 |
| Threshold Voltage Vth (V) | 2.60 |
| Minimum Steepness $\beta_{min}$ (—) | 1.24 |
| High Temp. Liquid Crystal Phase (60° C.) | |
| Low Temp. Liquid Crystal Phase (−20° C.) | |

Composition Examples 23, 24 and 25

Table 11 shows the composition and the characteristics of Composition Examples 23, 24 and 25 including the compound prepared by substituting the 5th or 5'th position of 2-phenylpyridine with benzene of cyclohexane through ethane combination as Compound A (the compound is hereinafter referred to as Compound A-II).

Compound A of Composition Example 23 is combined with a cyclohexane ring through ethane combination and the group at both ends is a straight chain alkyl group.

Compound A of Composition Example 24 is combined with a benzene ring through ethane combination and the group at one end is a straight chain alkyl group and the group at the other end is a straight chain alkoxy group.

The threshhold voltage of Composition Examples 23 and 24 was between about 2.9 and 3.0 V. These compositions both have excellent steepness $\beta$ which was 1.25 of 1.24.

Compound A of Composition Example 25 has a cyano group at one end. Such a compound has the characteristic to present a nematic phase wherein the dielectric constant parallel to the molecular axis is larger than the dielectric constant vertical to the molecular axis due to its structure (this is a so-called Np liquid crystal compound). Accordingly, Composition Example 25 including such compound as above had a lower threshhold voltage compared with Composition Examples 24 or 25.

Compound A-II has a high clear point (150° C. or higher) and consequently, the nematic liquid crystal composition including Compound A-II also has a high clear point. The clear point of Composition Examples 23 to 25 was 82.7° C. with a stable high temperature liquid crystal phase at 80° C. Furthermore, the low temperature liquid crystal phase was also improved and at −40° C., the composition presented a stable nematic liquid crystal phase in the cell. That is, if the nematic liquid crystal composition in accordance with this invention is used in a display unit, the unit can be driven or maintained over the wide range of temperature from 60° C. below and 60° C. above room temperature (which is defined to be 20° C.). Such a display unit is suitable for use in the harsh temperature condition such as in a car.

As mentioned above, by using Compound A-II, the steepness is improved and the liquid crystal temperature range is widened.

In Compound A-II, the 5th or 5'th position of 2-phenylpyridine is substituted with a benzene ring or a cyclohexane ring through an ethane combination. The groups at the end are preferably an alkyl group, an alkoxy group or a cyano group. Especially, in the case of an end group being a cyano group, the threshhold voltage is lowered. Moreover, as explained in the description of Composition Examples 3 to 6 and 8 to 17, the threshhold voltage may be arbitrarily selected by varying the concentration of Compound B.

TABLE 11

| | Composition (wt %) | Composition Example | | |
|---|---|---|---|---|
| | | 23 | 24 | 25 |
| A | C₃H₇—⟨H⟩—(CH₂)₂—⟨◯⟩—⟨◯N⟩—C₅H₁₁ | 10.0 | 0 | 0 |
| | C₅H₁₁—O—⟨◯⟩—⟨◯N⟩—(CH₂)₂—⟨◯⟩—C₄H₉ | 0 | 10.0 | 0 |

TABLE 11-continued
| | Composition (wt %) | Composition Example 23 | 24 | 25 |
|---|---|---|---|---|
| | 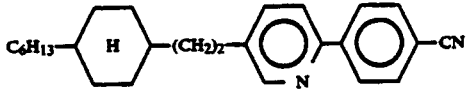 | 0 | 0 | 10.0 |
| B | 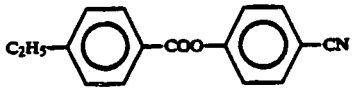 | 6.0 | 6.0 | 6.0 |
| | 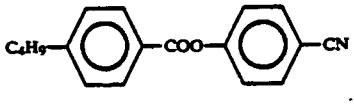 | 6.0 | 6.0 | 6.0 |
| C | 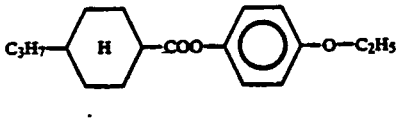 | 1.4 | 1.4 | 1.4 |
| | 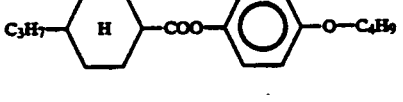 | 4.9 | 4.9 | 4.9 |
| |  | 3.6 | 3.6 | 3.6 |
| | 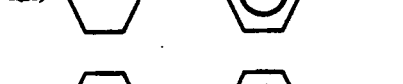 | 3.1 | 3.1 | 3.1 |
| |  | 3.8 | 3.8 | 3.8 |
| |  | 16.1 | 16.1 | 16.1 |
| |  | 3.9 | 3.9 | 3.9 |
| | 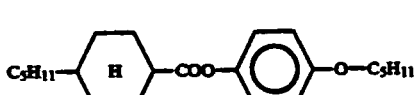 | 10.5 | 10.5 | 10.5 |
| | 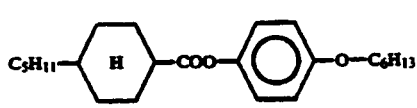 | 7.6 | 7.6 | 7.6 |
| |  | 14.5 | 14.5 | 14.5 |

TABLE 11-continued

| Composition (wt %) | Composition Example | | |
|---|---|---|---|
| | 23 | 24 | 25 |
| $C_6H_{13}$—H—COO—◯—O—$C_4H_9$ | 8.6 | 8.6 | 8.6 |
| Threshold Voltage Vth (V) | 3.02 | 2.87 | 2.54 |
| Minimum Steepness $\beta$min (—) | 1.25 | 1.24 | 1.25 |
| High Temp. Liquid Crystal Phase (80° C.) | | | |
| Low Temp. Liquid Crystal Phase (−40° C.) | | | |

Composition Examples 26, 27 and 28

Table 12 shows the composition and the characteristics of Composition Examples 26, 27 and 28 including at least one Compound A represented by the general formula:

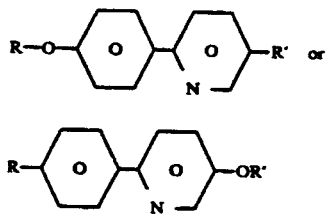

and at least one Compound C represented by the general formula:

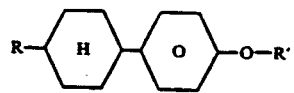

(the latter compound is hereinafter referred to as n—PCH).

By combining Compound A and n—PCH, a liquid crystal composition having an excellent steepness value is obtained. Specifically, Composition Examples 27 and 28 including Compound A in a large amount present an excellent steepness $\beta$ of 1.22.

The birefringence $\Delta n$ of n-PCH itself is as small, for example about 0.09. However, the viscosity thereof at 20° C. is about 30 centipoise (hereinafter referred to as cP), which is very small. n-PCH contributes to shorten the response speed of the composition. For example, Composition Example 28 has a very short response time T of 170 ms.

TABLE 12

| | Composition (wt %) | Composition Examples | | |
|---|---|---|---|---|
| | | 26 | 27 | 28 |
| A | $C_5H_{11}$—O—◯—◯(N)—$C_5H_{11}$ | 20.0 | 30.0 | 10.0 |
| | $C_6H_{13}$—O—◯—◯(N)—$C_5H_{11}$ | 0 | 0 | 10.0 |
| | $C_6H_{13}$—O—◯—◯(N)—$C_5H_{11}$ | 0 | 0 | 10.0 |
| | $C_5H_{11}$—O—◯—◯(N)—$C_5H_{11}$ | 0 | 0 | 10.0 |
| B | $C_2H_5$—◯—COO—◯—CN | 6.2 | 6.0 | 6.1 |
| | $C_4H_9$—◯—COO—◯—CN | 6.2 | 5.0 | 6.1 |

TABLE 12-continued

| Composition (wt %) | Composition Examples | | |
|---|---|---|---|
| | 26 | 27 | 28 |
|  $C_3H_7$—◯—◯—CN | 0 | 4.0 | 0 |
|  $C_5H_{11}$—◯—◯—CN | 0 | 4.0 | 0 |
| C 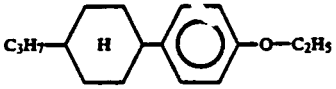 $C_3H_7$—H—◯—O—$C_2H_5$ | 9.3 | 7.9 | 6.1 |
|  $C_3H_7$—H—◯—O—$C_4H_9$ | 9.2 | 7.8 | 6.0 |
|  $C_3H_7$—H—◯—O—$C_5H_{11}$ | 10.3 | 9.7 | 6.7 |
|  $C_4H_9$—H—◯—O—$CH_3$ | 6.5 | 4.6 | 3.6 |
|  $C_4H_9$—H—◯—O—$C_2H_5$ | 7.0 | 5.1 | 3.9 |
|  $C_5H_{11}$—H—◯—O—$C_2H_5$ | 9.1 | 6.9 | 5.3 |
| D  $C_5H_{11}$—H—◯—◯—H—$C_3H_7$ | 16.2 | 0 | 16.2 |
| 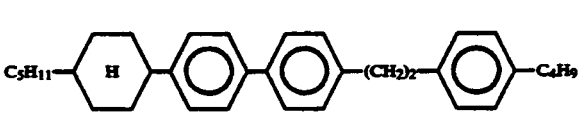 $C_5H_{11}$—H—◯—◯—$(CH_2)_2$—◯—$C_4H_9$ | 0 | 10.0 | 0 |
| Threshold Voltage Vth (V) | 2.56 | 2.28 | 2.97 |
| Minimum Steepness βmin (—) | 1.25 | 1.22 | 1.22 |
| High Temp. Liquid Crystal Phase (60° C.) | | | |
| Low Temp. Liquid Crystal Phase (−40° C.) | | | |

Composition Examples 29 and 30

Table 13 shows the compositions and the characteristics of Composition Examples 29 and 30 including the compound prepared by substituting the 5th or 5'th position of 2-phenylpyridine with benzene or cyclohexane through an ethane combination and n-PCH as Compounds C.

The steepness value for these Examples 29 and 30 are 1.22 and 1.23, respectively and are very excellent. The response speed is quick, for example, the response speed of Example 29 is 217 ms.

The clear points of Composition Examples 29 and 30 are 90.9° C. and 91.2° C., respectively, which are both very high. So, the high temperature liquid crystal phase at 90° C. is stable. With respect to Example 29, the low temperature liquid crystal phase at −40° C. is good. Composition Example 30, on the other hand, presents the nematic phase until about −30° C. At −40° C., the smectic phase is presented and the composition is not driven at such temperature. However, when the composition is sealed in a cell, even at −40° C., deposition which damages the cell does not occur, and the cell can be stored without being damaged.

Composition Example 31

Table 14 shows Composition Example 31 including the compound represented by the general formula:

TABLE 13

| Composition (wt %) | Composition Example | |
|---|---|---|
| | 29 | 30 |
| A 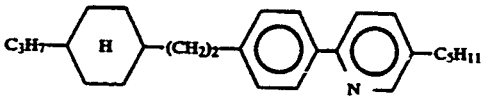 | 20.0 | 0 |
| 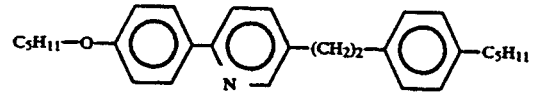 | 0 | 20.0 |
| B 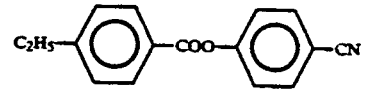 | 6.1 | 6.1 |
| 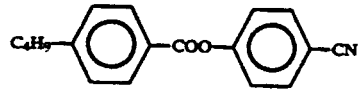 | 6.1 | 6.1 |
| C  | 9.4 | 9.4 |
| 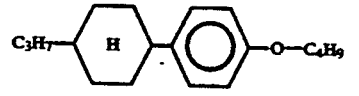 | 9.3 | 9.3 |
| 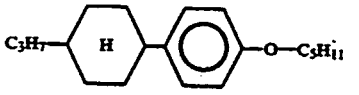 | 10.3 | 10.3 |
| 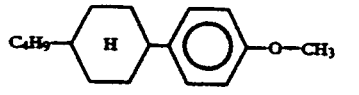 | 6.5 | 6.5 |
| 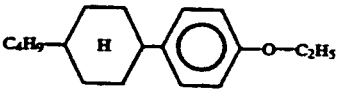 | 7.0 | 7.0 |
| 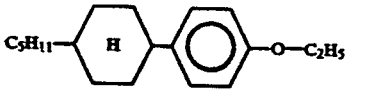 | 9.1 | 9.1 |
| D  | 16.2 | 16.2 |
| Threshold Voltage Vth (V) | 2.96 | 2.73 |
| Minimum Steepness βmin (—) | 1.22 | 1.23 |
| High Temp. Liquid Crystal Phase (90° C.) | | |
| Low Temp. Liquid Crystal Phase (−30° C.) | | |
| Low Temp. Liquid Crystal Phase (−40° C.) | | Sm |

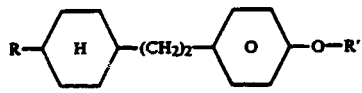

(hereinafter referred to as CAPO) as Compound C in combination with n−PCH.

The viscosity of CAPO is about 10cP, which is very small (Reference: M. Schadt, M. Petrzilka, P. R. Gerber, A. Villiger and G. Trickes, Mol. Cryst. Liq. Chryst., Vol. 94 pp 139–153, 1983). Accordingly, CAPO has the same effect with respect to the response speed as n−PCH.

This example is also good in the steepness $\beta$, which is 1.24.

TABLE 14

| Composition (wt %) | Composition Example 31 |
|---|---|
| A | 10.0 |
| B | 6.3 |
|   | 7.2 |
| C | 8.1 |
|   | 8.1 |
|   | 5.4 |
|   | 5.4 |
|   | 13.5 |
|   | 4.5 |
|   | 9.0 |
|   | 18.0 |

TABLE 14-continued

| Composition (wt %) | Composition Example 31 |
|---|---|
| 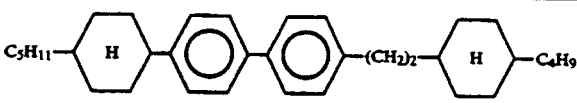 | 4.5 |
| Threshold Voltage Vth (V) | 2.21 |
| Minimum Steepness βmin (—) | 1.24 |
| High Temp. Liquid Crystal Phase (50° C.) | |
| Low Temp. Liquid Crystal Phase (−10° C.) | |

Composition Examples 32 and 33

Table 15 and Table 16 show the compositions and the characteristics of Composition Examples 32 and 33, respectively. These Composition Examples include as Compound C, the ester compounds represented by the general formula:

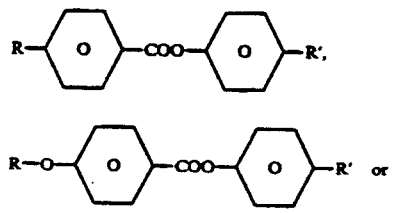

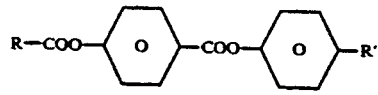

(hereinafter referred to as n−E). n−E has a high birefringence Δn of about 0.15 and a clear point as high as about 80° C. They present stable nematic liquid crystal phase over a relatively wide temperature range. Accordingly, by combining n−E and Compound A, the steepness β of the composition is improved with maintaining the property of n−E.

TABLE 15

| Composition (wt %) | Composition Example 32 |
|---|---|
| A $C_6H_{13}-O-\bigcirc-\bigcirc_N-C_5H_{11}$ | 10.0 |
| B $C_2H_5-\bigcirc-COO-\bigcirc-CN$ | 5.0 |
| $C_4H_9-\bigcirc-COO-\bigcirc-CN$ | 5.0 |
| C $C_5H_{11}-\bigcirc-COO-\bigcirc-C_3H_7$ | 8.0 |
| $CH_3-O-\bigcirc-COO-\bigcirc-C_5H_{11}$ | 12.4 |
| $C_6H_{13}-O-\bigcirc-COO-\bigcirc-C_5H_{11}$ | 12.4 |

TABLE 15-continued

| Composition (wt %) | Composition Example 32 |
|---|---|
| 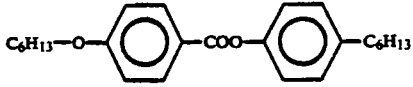 $C_6H_{13}$—O—⬡—COO—⬡—$C_6H_{13}$ | 12.4 |
| 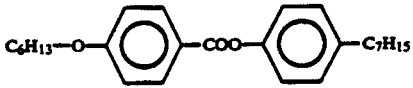 $C_6H_{13}$—O—⬡—COO—⬡—$C_7H_{15}$ | 12.4 |
| 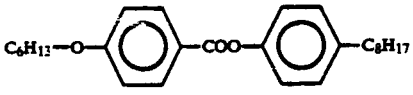 $C_6H_{13}$—O—⬡—COO—⬡—$C_8H_{17}$ | 12.4 |
| D  $C_5H_{11}$—⬡H—⬡—⬡—⬡H—$C_3H_7$ | 10.0 |
| Threshold Voltage Vth (V) | 3.12 |
| Minimum Steepness β min | 1.26 |
| High Temp. Liquid Crystal Phase (50° C.) | |
| Low Temp. Liquid Crystal Phase (−10° C.) | |

TABLE 16

| Composition (wt %) | Composition Example 33 |
|---|---|
| A  $C_6H_{13}$—O—⬡—⬡N—$C_5H_{11}$ | 10.0 |
| B 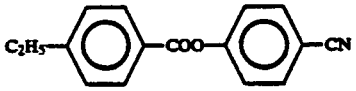 $C_2H_5$—⬡—COO—⬡—CN | 5.0 |
| 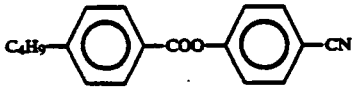 $C_4H_9$—⬡—COO—⬡—CN | 5.0 |
| C 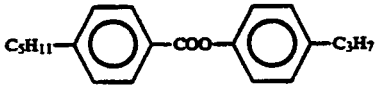 $C_5H_{11}$—⬡—COO—⬡—$C_3H_7$ | 17.5 |
| 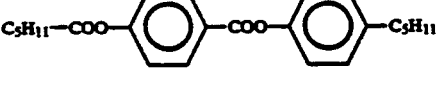 $C_5H_{11}$—COO—⬡—COO—⬡—$C_5H_{11}$ | 17.5 |
| 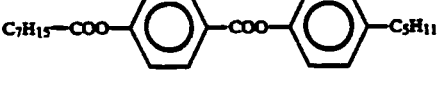 $C_7H_{15}$—COO—⬡—COO—⬡—$C_5H_{11}$ | 17.5 |
| 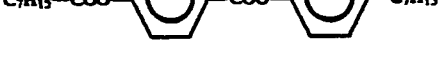 $C_7H_{15}$—COO—⬡—COO—⬡—$C_7H_{15}$ | 17.5 |

TABLE 16-continued

| Composition (wt %) | Composition Example 33 |
|---|---|
| D  $C_5H_{11}$—⟨H⟩—⟨⟩—⟨⟩—⟨H⟩—$C_3H_7$ | 10.0 |
| Threshold Voltage Vth (V) | 2.94 |
| Minimum Steepness β min (—) | 1.25 |
| High Temp. Liquid Crystal Phase (50° C.) | |
| Low Temp. Liquid Crystal Phase (—10° C.) | |

Composition Example 34

Table 17 shows the composition and the characteristics of Composition Example 34.

As mentioned in the description of Composition Example 1, the compound represented by the general formula:

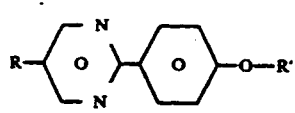

(hereinafter referred to as n—P) has the most acceptable characteristics among the liquid crystal compounds generally used, such as a relatively large Δn and a small elasticity ratio $K_{33}/K_{11}$.

Similar to the compositions of Examples 32 and 33, by combining n—P and Compound A, the steepness and the response time of the composition are greatly improved and the liquid crystal temperature range is expanded.

TABLE 17

| Composition (wt %) | Composition Example 34 |
|---|---|
| A  $C_6H_{13}$—O—⟨⟩—⟨N⟩—$C_5H_{11}$ | 10.0 |
| B  $C_2H_5$—⟨⟩—COO—⟨⟩—CN | 5.0 |
| $C_4H_9$—⟨⟩—COO—⟨⟩—CN | 5.0 |
| C  $C_4H_9$—⟨N,N⟩—⟨⟩—O—$C_4H_9$ | 7.0 |
| $C_5H_{11}$—⟨N,N⟩—⟨⟩—O—$C_4H_9$ | 10.5 |
| $C_5H_{11}$—⟨N,N⟩—⟨⟩—O—$C_5H_{11}$ | 14.0 |
| $C_5H_{11}$—⟨N,N⟩—⟨⟩—O—$C_6H_{13}$ | 14.0 |

TABLE 17-continued

| Composition (wt %) | Composition Example 34 |
|---|---|
| 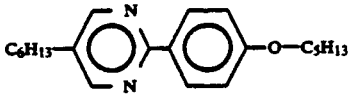 | 7.0 |
| 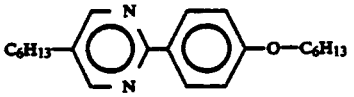 | 17.5 |
| D  | 10.0 |
| Threshold Voltage Vth (V) | 2.57 |
| Minimum Steepness β min | 1.22 |
| High Temp. Liquid Crystal Phase (60° C.) | |
| Low Temp. Liquid Crystal Phase (−20° C.) | — |

Composition Examples 35 and 36

Table 18 shows the compositions and the characteristics of Composition Examples 35 and 36. These examples show that addition of 2-phenylpyridine derivatives in accordance with the invention is effective for providing a liquid crystal phase for compounds other than Compounds A, B, C and D.

For example, the compound represented by the general formula:

presents a liquid crystal phase when added to the liquid crystal compositions in accordance with this invention in spite of the fact that the compound does not present a nematic liquid crystal phase as a single compound and has a wax-like solid state. The biphenyl-like molecular shape of this compound has almost a planar structure so that regular alignment is easily attained, thereby presented the stable solid phase. However, since the shape of the molecules as a whole is long and thin, when it is added to a liquid crystal composition in accordance with the invention the stable liquid crystal phase is maintained.

TABLE 18

| Composition (wt %) | | Composition Example 35 | Composition Example 36 |
|---|---|---|---|
| A |  | 5.0 | 10.0 |
| B | 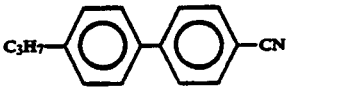 | 6.6 | 6.3 |
| |  | 7.6 | 7.2 |
| C | 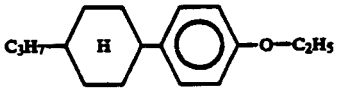 | 15.6 | 14.8 |
| | 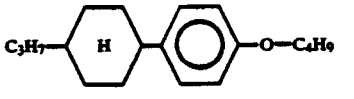 | 15.7 | 14.9 |

TABLE 18-continued

| Composition (wt %) | Composition Example | |
|---|---|---|
| | 35 | 36 |
| $C_4H_9$—H—⬡—O—$C_2H_5$ | 10.4 | 9.9 |
| $C_5H_{11}$—H—⬡—O—$CH_3$ | 10.5 | 9.9 |
| D $C_5H_{11}$—H—⬡—⬡—$C_2H_5$ | 14.2 | 13.5 |
| $C_5H_{11}$—H—⬡—⬡—H—$C_3H_7$ | 4.8 | 4.5 |
| $C_5H_{11}$—⬡—⬡—$C_4H_9$ | 4.8 | 4.5 |
| $C_5H_{11}$—⬡—⬡—$C_3H_7$ | 4.8 | 4.5 |
| Threshold Voltage Vth (V) | 2.81 | 2.92 |
| Minimum Steepness β min (−) | 1.22 | 1.23 |
| High Temp. Liquid Crystal Phase (40° C.) | | |
| Low Temp. Liquid Crystal Phase (0° C.) | | |

Composition Example 37

Conventional Composition 37 and Composition Example 37 including the compounds as listed below respectively were prepared.

| Conventional Composition 37 | |
|---|---|
| Compounds | Amount |
| 4-α-propylcyclohexyl-1-carboxylic acid 4-ethoxyphenylester | 8.94 (wt %) |
| 4-α-propylcyclohexyl-carboxylic acid 4-α-butoxyphenylester | 17.88 (wt %) |
| 4-α-butylcyclohexyl-1-carboxylic acid 4-ethoxyphenylester | 18.56 (wt %) |
| 4-α-pentyl-4'-cyanoterphenyl | 6.24 (wt %) |
| 4-ethylbenzoic acid 4-cyanophenylester | 12.25 (wt %) |
| 4-butylbenzoic acid 4-cyanophenylester | 12.25 (wt %) |
| 4-(2-methylbutyl)-4'-cyanobiphenyl | 0.5 (wt %) |
| melting point 5° C., clear point 67.2° C. | |

| Composition Example 37 | |
|---|---|
| Compounds | Amount |
| Composition A | 80 (wt %) |
| 2-(4-ethoxyphenyl)-5-pentylpyridine | 6.8 (wt %) |
| 2-(4-pentyloxyphenyl)-5-pentylpyridine | 6.6 (wt %) |
| 2-(4-hexyloxyphenyl)-5-pentylpyridine | 6.6 (wt %) |
| melting point 5° C., clear point 64.5° C. | |

Each of Conventional Composition 37 and Composition Example 37 were sealed into TN cells having a thickness of 10 m. The TN cells were driven by the alternative current status driving mode and the voltage-brightness property (see FIG. 2) of each TN cell at 25° C. was measured. The results are shown in Table 19.

Table 19

| Composition | $V_{10}$ | τr (ms) | τd (ms) | α | β |
|---|---|---|---|---|---|
| Conventional | 1.667 | 100.2 | 178.8 | 1.264 | 1.343 |
| Example 37 | 1.889 | 93.6 | 169.6 | 1.242 | 1.358 |

As shown in Table 19, $V_{10}$ is the voltage when the light transmittance is 10%, τ r and τ d are the response times at rise and fall. τ r and τ d are measured from an observing direction $θ=90°$ of the TN cell. α and β are the factors indicating the visual angle dependence and the threshhold property, respectively and defined as below and shown in FIG. 2:

$α=90° V50/50° V50$ $β=90° V10/90° V90$

As described herein, in accordance with this invention, by adjusting liquid crystal compositions by including at least one 2-phenylpyridine derivatives presented by the general formula:

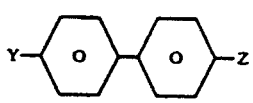

the steepness value of the composition was dramatically improved and provides a composition which is well suited to the dynamic driving mode. Many other advantages are obtained. For example, the birefringence Δn is increased and the response speed is improved by reducing the ratio between viscosity and elasticity. The liquid crystal temperature range is between 20° C. above and below room temperature (20° C.) at the narrowest and between 60° C. above and below room temperature at widest. Additionally, the threshhold voltage can be varied as desired.

The compounds used in this invention are all chemically stable against light, heat, humidity and so on. Accordingly, the liquid crystal composition including such compounds have suitable characteristics for the dynamic driving mode. They are especially effective when used in the display unit of the twisted nematic type and in the display unit as the host liquid crystal of the guest-host type. Moreover, the liquid crystal compositions in accordance with this invention are also applicable to the various display units as the cholesteric-nematic phase transition type liquid crystal or the liquid crystal material for the double-frequency driving mode, by adding cholesteric liquid crystal compound or the liquid crystal compound having the large frequency-dependence of the dielectric constant, respectively.

It will thus be seen that the objects set forth above, among those made apparent from the preceding description, are efficiently attained and, since certain changes may be made in carrying out the above embodiments and in the compositions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. 2-phenylpyridine derivatives represented by the general formula:

wherein one of Y and Z is

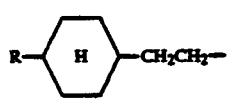

and when Y is

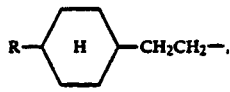

Z is one of R— and —CN; and when Z is

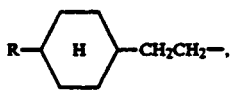

Y is one of —R or —CN; and R is a straight chain alkyl group from 1 to 12 carbon atoms.

2. A nematic liquid crystal composition comprising an effective amount of at least one 2-phenylpyridine derivative having the general formula:

wherein one of Y and Z is

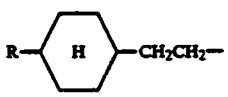

and when Y is

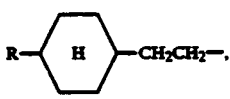

Z is one of R— and —CN; and when Z is

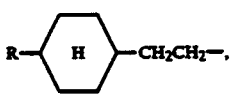

Y is one of —R or —CN; and R is a straight chain alkyl group from 1 to 12 carbon atoms, for reducing the steepness and response time of the liquid crystal composition.

3. The liquid crystal composition of claim 2, wherein the 2-phenylpyridine derivative is present in the composition in an amount between about 2 and 80wt%, based on the total weight of the composition.

4. The liquid crystal composition of claim 2, wherein the 2-phenylpyridine derivative is present in the composition in an amount between about 10–30wt%, based on the total weight of the composition.

5. The liquid crystal composition of claim 2, wherein the 2-phenylpyridine derivative is present in the composition in an amount of about 20wt%, based on the total weight of the composition.

6. The liquid crystal composition of claim 4, wherein the composition includes compounds having a negative dielectric anisotropy and compounds having a positive dielectric anisotropy.

7. A liquid crystal display device, comprising two spaced apart substrates, at least one of which is transparent, the interior surfaces of the substrates having electrodes disposed thereon with a spacer between the substrates for forming an interior space between the substrates, a liquid crystal composition disposed in the space between the substrates, the liquid crystal composition comprising a nematic liquid crystal composition including at least one 2-phenylpyridine derivative having the following general formula:

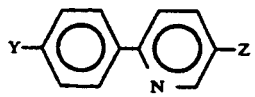

wherein one of Y and Z is

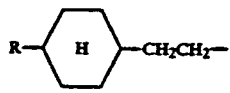

and when Y is

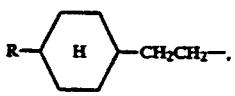

Z is one of R— and —CN; and when Z is

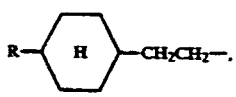

Y is one of —R or —CN; and R is a straight chain alkyl group from 1 to 12 carbon atoms.

8. 2-phenylpyridine derivatives represented by the general formula:

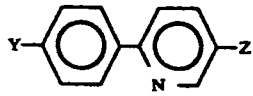

wherein Y is

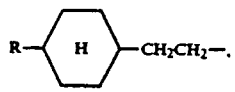

Z is R and R is a straight chain alkyl group from 1 to 12 carbon atoms.

9. 2-phenylpyridine derivatives represented by the general formula:

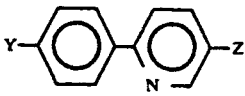

wherein Y is

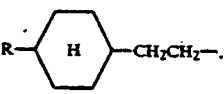

Z is —CN and R is a straight chain alkyl group from 1 to 12 carbon atoms.

10. 2-phenylpyridine derivatives represented by the general formula:

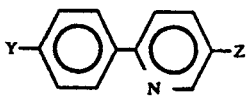

wherein Y is R, Z is

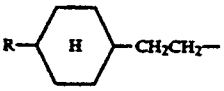

and R is a straight chain alkyl group from 1 to 12 carbon atoms.

11. 2-phenylpyridine derivatives represented by the general formula:

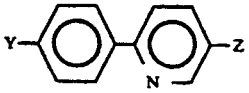

wherein Y is —CN, Z is

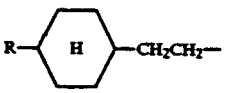

and R is a straight chain alkyl group from 1 to 12 carbon atoms.

* * * * *